US009626758B2

(12) United States Patent
Taylor et al.

(10) Patent No.: US 9,626,758 B2
(45) Date of Patent: Apr. 18, 2017

(54) INTEGRATION OF MEDICAL SOFTWARE AND ADVANCED IMAGE PROCESSING

(71) Applicant: TeraRecon, Inc., Foster City, CA (US)

(72) Inventors: Robert James Taylor, San Francisco, CA (US); Tiecheng Zhao, Concord, MA (US); Tim Frandsen, Germantown, TN (US)

(73) Assignee: TeraRecon, Inc., Foster City, CA (US)

( * ) Notice: Subject to any disclaimer, the term of this patent is extended or adjusted under 35 U.S.C. 154(b) by 189 days.

(21) Appl. No.: 14/533,079

(22) Filed: Nov. 4, 2014

(65) Prior Publication Data

US 2015/0055838 A1 Feb. 26, 2015

Related U.S. Application Data

(63) Continuation of application No. 13/683,868, filed on Nov. 21, 2012, now Pat. No. 8,908,947.

(60) Provisional application No. 61/649,427, filed on May 21, 2012, provisional application No. 61/681,921, filed on Aug. 10, 2012.

(51) Int. Cl.
  *G06K 9/00* (2006.01)
  *G06T 7/00* (2017.01)
  *G06F 19/00* (2011.01)

(52) U.S. Cl.
  CPC .......... *G06T 7/0012* (2013.01); *G06F 19/321* (2013.01); *G06F 19/322* (2013.01)

(58) Field of Classification Search
  None
  See application file for complete search history.

(56) References Cited

U.S. PATENT DOCUMENTS

| 5,452,416 A | 9/1995 | Hilton et al. |
| 6,614,873 B1 | 9/2003 | Taylor et al. |
| 7,180,624 B2 | 2/2007 | Tipirneni |
| 7,564,579 B2 | 7/2009 | Tipirneni |
| 7,583,861 B2 | 9/2009 | Hanna et al. |

(Continued)

OTHER PUBLICATIONS

New vessel analysis tool for morphometric qualification and visualization of vessels in CT and MR imaging data sets, by Boskamp, RadioGraphics-2004, pp. 287-297.*

(Continued)

*Primary Examiner* — Vikkram Bali
(74) *Attorney, Agent, or Firm* — Blakely, Sokoloff, Taylor & Zafman LLP

(57) ABSTRACT

According to one embodiment, at least a portion of medical information of a patient is displayed within MRCS executed within a local device, the medical information including medical treatment history of the patient. At least a portion of the displayed medical information of the patient is transmitted to a medical imaging processing server over a network, where the transmitted medical information includes a patient identifier (ID) of the patient. Both the at least a portion of patient medical information and one or more medical images are displayed within the MRCS, where the medical images are associated with the patient and rendered by the medical image processing server. A set of icons representing a set of image processing tools is displayed within the MRCS, which when activated by a user, allow an image to be manipulated by the imaging processing server.

24 Claims, 21 Drawing Sheets

(56) References Cited

U.S. PATENT DOCUMENTS

| | | | |
|---|---|---|---|
| 7,660,413 B2 | 2/2010 | Partovi et al. |
| 7,660,488 B2 | 2/2010 | Reicher et al. |
| 7,716,072 B1 | 5/2010 | Green et al. |
| 7,756,724 B2 | 7/2010 | Gropper et al. |
| 7,787,672 B2 | 8/2010 | Reicher et al. |
| 7,860,287 B2 | 12/2010 | Zahlmann et al. |
| 7,936,908 B2 | 5/2011 | Brackett |
| 7,953,614 B1 | 5/2011 | Reicher et al. |
| 7,970,625 B2 | 6/2011 | Reicher et al. |
| 8,059,297 B2 | 11/2011 | Tipirneni |
| 8,065,166 B2 | 11/2011 | Maresh et al. |
| 8,094,901 B1 | 1/2012 | Reicher et al. |
| 8,370,293 B2 | 2/2013 | Iwase et al. |
| 8,682,049 B2 | 3/2014 | Zhao et al. |
| 8,731,961 B2 | 5/2014 | Hanina et al. |
| 2004/0257608 A1 | 12/2004 | Tipirneni |
| 2005/0148849 A1 | 7/2005 | Heere et al. |
| 2005/0267351 A1 | 12/2005 | Humphrey et al. |
| 2006/0031093 A1 | 2/2006 | Serrano et al. |
| 2006/0093207 A1 | 5/2006 | Reicher et al. |
| 2006/0190999 A1 | 8/2006 | Chen et al. |
| 2006/0229911 A1 | 10/2006 | Gropper et al. |
| 2006/0230072 A1 | 10/2006 | Partovi et al. |
| 2007/0005798 A1 | 1/2007 | Gropper et al. |
| 2007/0027715 A1 | 2/2007 | Gropper et al. |
| 2007/0075135 A1 | 4/2007 | Dettinger et al. |
| 2007/0192140 A1 | 8/2007 | Gropper |
| 2007/0237380 A1 | 10/2007 | Iwase et al. |
| 2008/0025583 A1 | 1/2008 | Jabri et al. |
| 2009/0103789 A1 | 4/2009 | Danner et al. |
| 2009/0281839 A1 | 11/2009 | Lynn et al. |
| 2010/0049740 A1 | 2/2010 | Iwase et al. |
| 2010/0122336 A1 | 5/2010 | Hunt et al. |
| 2010/0135554 A1 | 6/2010 | Kohlmann et al. |
| 2010/0146044 A1 | 6/2010 | Holmes et al. |
| 2011/0110568 A1 | 5/2011 | Vesper et al. |
| 2011/0153351 A1 | 6/2011 | Vesper et al. |
| 2011/0166890 A1 | 7/2011 | Menschik et al. |
| 2012/0002853 A1 | 1/2012 | Omernick et al. |
| 2012/0035954 A1 | 2/2012 | Yeskel |
| 2012/0041786 A1 | 2/2012 | Yu |
| 2012/0163684 A1 | 6/2012 | Natanzon et al. |
| 2012/0194540 A1 | 8/2012 | Reicher et al. |

OTHER PUBLICATIONS

International Search Report and Written Opinion mailed Jul. 29, 2013, for International Patent Application No. PCT/US2013/042088, 13 pages.

Elmar Kotter et al., "Technologies for image distribution in hospitals," European Radiology, Springer, Berlin, Germany, vol. 16, No. 6, Mar. 10, 2006.

Munch, H. et al. "The integration of medical images with the electronic patient record and their web-based distribution," Academic Radiology, Reston, VA, US, vol. 11, No. 6, Jun. 1, 2004.

Ruth E. Dayhoff et al., "Providing complete multimedia patient data to consulting radiologists, other specialists, and the referring clinician," Journal of Digital Imaging; The Journal of the Society for Computer Applications in Radiology, Springer-Verlag, NE, vol. 11, No. 1, Aug. 1, 1998.

Steve G. Langer "Architecture of an image capable, web-based, electronic medical record," Journal of Digital Imaging; The Journal of the Society for Computer Applications in Radiology, Springer-Verlag, NE, vol. 13, No. 2, Feb. 1, 2000.

"IHE Cardiology Technical Framework Supplement: Image-Enabled Office (IEO) Integration Profile," IHE Cardiology Technical Committee (2009-2010); IHE International, Inc., Jul. 30, 2010, 47 pages.

PCT/US2013/042088, International Preliminary Report on Patentability, Dec. 4, 2014, 9 pages.

\* cited by examiner

INTEGRATION OF MEDICAL SOFTWARE AND ADVANCED IMAGE PROCESSING

RELATED APPLICATIONS

This application is a continuation of U.S. application Ser. No. 13/683,868, filed Nov. 21, 2012, which claims the benefit of U.S. Provisional Application No. 61/649,427, filed May 21, 2012 and U.S. Provisional Application No. 61/681,921, filed Aug. 10, 2012, which are incorporated by reference herein.

FIELD OF THE INVENTION

Embodiments of the present invention relate generally to integrated medical software systems. More particularly, embodiments of the invention relate to integration of image(s) and/or image processing with medical software.

BACKGROUND

As medical software becomes more sophisticated and universal, integration among software packages becomes more important and more challenging. For example, electronic medical records (EMR) or electronic health records (EHR) are becoming increasingly common. Clinical trials software, dictation software, research software, radiology information system (RIS) software, Hospital Information System (HIS) software, picture archiving and communication system (PACS) software are other examples of increasingly common medical software.

One of the challenges of the increased use of these different software packages is that they are generally created and supported by different vendors, and do not interoperate or "talk" to each other well. But, when a physician, technician or administrator is dealing with a patient, he/she needs to access all of the information that is pertinent to that patient easily and without having to actively open several different software packages, search for the patient, and then search for the patient's information that is pertinent.

It is particularly important to be able to view, and where necessary, manipulate, images that are associated with a particular patient and/or condition. This is important whether the patient is being treated for a condition, having a regular checkup, or participating in a clinical trial/study.

For example, if a patient is being treated for cancer, his EMR needs to show what medications he is on, what procedures he has had and is scheduled to have, and it also needs to show his progress. The location and size of his cancer, as well as his progress are most likely best depicted in images, whether they are scan images (CT, MRI, Ultrasound etc.) or simple X-ray images or other images, such as lab images or photographs (for example, of skin cancer), etc. It is also likely that the physician for this patient will want to do more than simply view the images. He/she may want to change the settings for the images (for example, the window and/or level settings), zoom, pan, measure, view the images from different angles, view the images in a 3D model, rotate the 3D model, segment the images, perform measurements or anatomy identification on the model/images, etc., to better assess the patient's condition.

Currently this is not practical within any of the EMR or EHR software packages. Some EMR software allows the user to view a static image, such as an X-ray, but the user is not able to manipulate the image, or view a more advanced image such as a 3D image with appropriate interactive tools. Software packages exist for doing this more advanced image processing, but currently they are not integrated with EMR or other medical software platforms. This is not a trivial task since advanced image processing software must handle vast amounts of data and deliver processing power that is well beyond the capacity of most other types of software packages. The same lack of integration exists for clinical trials, and other medical software packages also.

From here on, EMR, EHR, and other medical record software will be referred to collectively as medical record software (MRS). Clinical trial or other trial software will be referred to collectively as clinical trial software (CTS). The term medical record and/or clinical trial software (MRCS) will be used to refer to CTS and/or MRS or other medical software where integration with medical images is desired.

There is a need for seamless integration of MRCS packages with medical images and/or advanced image processing. A user does not want to launch a separate imaging application while using an MRCS software package. The user wants to simply be able to view and manipulate, if necessary, the images associated with that particular patient, while using the MRCS. For example, a cardiologist looking at patient X's EMR wants to see only patient X's cardiovascular images and only the cardiology tools that correspond to them. The cardiologist does not want to have to search through multiple patients, choose patient X, then search through Patient X's images to find the ones that pertain to cardiology, and then weed through multiple irrelevant tools to find the cardiology tools.

BRIEF DESCRIPTION OF THE DRAWINGS

Embodiments of the invention are illustrated by way of example and not limitation in the figures of the accompanying drawings in which like references indicate similar elements.

FIGS. 4A-4G are screenshots illustrates a graphical user interface of medical record software according to one embodiment of the invention.

FIGS. 5A-5D are screenshots illustrates a graphical user interface of clinical trial software according to one embodiment of the invention.

DETAILED DESCRIPTION

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment.

According to some embodiments, embodiments of the invention provide for the integrating of images and/or image processing with MRCS, including EMR, clinical trials software, dictation software, research software, radiology information system (RIS) software, picture archiving and communication system (PACS) software and other medical software packages. In one embodiment, advanced image processing is tightly integrated with a MRCS program. Integration can take the form of the image(s) and/or image processing tools showing up in the same window as the MRCS. Integration can also take the form of a window containing the image(s) and/or image processing tools opening up in a separate window from the MRCS window. In another embodiment the image processing software is integrated with the MRCS program and also opens up "in context." "In context" means that the image processing software opens up to show the appropriate image(s) and/or tools for the current user and/or patient and/or affliction.

Figure 1:
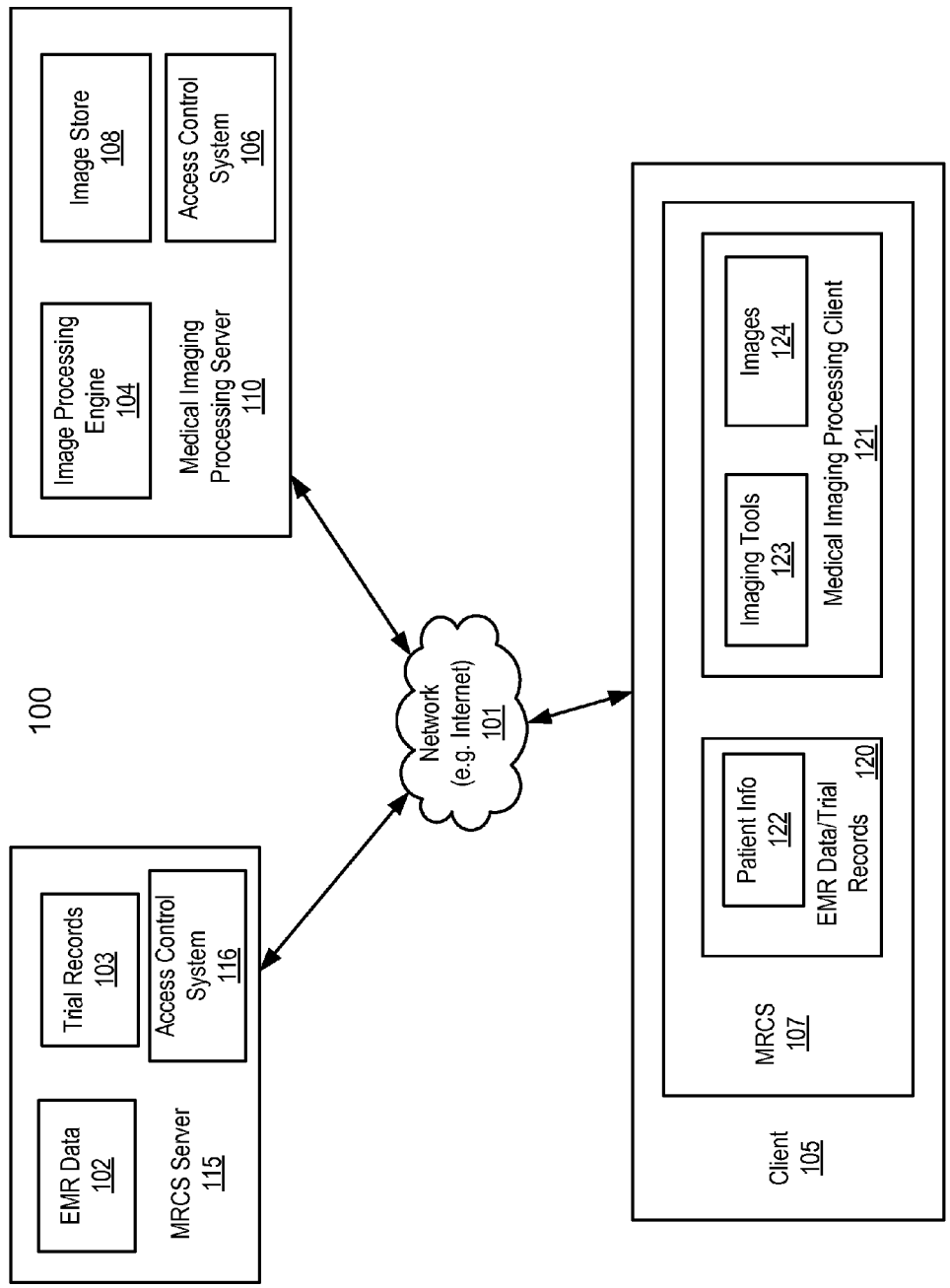
FIG. 1 is a block diagram illustrating an integrated medical software system according to one embodiment.

FIG. 1 is a block diagram illustrating integrated MRCS and advanced imaging processing system according to one embodiment. Referring to FIG. 1, according to one embodiment, system 100 includes a client 105 communicatively coupled to a medical imaging processing server 110 and medical data server 115 over a network 101, wired and/or wirelessly. Network 101 may be a local area network (LAN), a metropolitan area network (MAN), a wide area network (WAN) such as the Internet or an intranet, a private cloud network, a public cloud network, or a combination thereof. Although FIG. 1 illustrates a single client 105 communicatively coupled to the medical imaging processing server 110 and medical data server 115, it will be appreciated that multiple such clients may be communicatively coupled to the medical imaging processing server 110 and/or MRCS server 115.

MRCS server 115, in one embodiment, may be a data server that resides physically in a different location from the medical imaging processing server 110 and the client 105. In another embodiment, the MRCS server 115 may be in the same location as the medical imaging processing server 110 and/or client 105. MRCS server 115 may be operated by the same or different organization from client 105 and/or imaging processing server 110. In one embodiment, the MRCS server 115 includes data storage to store medical records of patients such as EMRs or EHRs 102. MRCS server 115 may also store clinical trial records 103 of anonymous patients. MRCS server 115 further includes access control system 116 for providing access to EMR Data 102 and trial records 103. Different users having different roles may be allowed to access different data. For example, a doctor may be allowed to access EMR data 102, while a medical student or professor may be allowed to access only the trial records 103. For the purpose of illustration, MRCS server 115 may represent a MRS server, a CTS server, or a combination of both and MRCS sever 115 may be implemented in a single server or a cluster of servers. Also note that MRCS server 115 may represent two separate serves: 1) a MRS server having EMR data 102 stored therein; and 2) a CTS server having trial records 103 stored therein.

Medical imaging processing server 110 includes an image processing engine which is configured to provide medical image processing services to client 105 over a network. In one embodiment, the medical imaging processing server 110 also includes an image store 108 to store medical data such as digital imaging and communications in medicine (DICOM) compatible data or other image data, including jpeg, TIFF, video, EKG, laboratory images, pdf, sound, and other files. The image store 108 may also incorporate encryption capabilities, where the medical data can be stored and transmitted in an encrypted form. The image store 108 may include multiple databases, and may be implemented with relational database management systems (RDBMS), e.g., Oracle™ database or Microsoft® SQL Server, etc. In one embodiment, the medical imaging processing server 110 includes an access control system 106 to control access, by the client 105, of resources (e.g., image processing tools) and/or medical data stored in image store. Client 105 may or may not access certain portions of resources and/or medical data stored in image store depending upon its access privilege. The access privileges may be determined or configured based on a set of role-based rules or policies. For example, client 105 may be configured with certain roles that only permit access to some of the tools provided by the medical imaging processing server 110. In other instances, client 105 may be configured with certain roles that limit its access to some patient information. For example, certain users (e.g., doctors, medical students) of client 105 may have different access privileges to access different medical information stored in image store 108 or different imaging rendering resources provided by imaging processing server 110.

Client 105 is a client which includes integrated medical software 107 as described herein. In one embodiment, the integrated software 107 integrates image(s) and/or image processing functionality 121 with medical record software (MRS) and/or clinical trial software (CTS) 107, which herein are collectively referred to as medical record and/or clinical software (MRCS). For example, imaging processing function may be implemented as a medical imaging processing client 121 communicatively coupled to image processing server 110 over network 101. Imaging processing client 121 may be linked to medical software 107 or embedded within medical software 107.

MRS is patient-centric software that focuses on medical records of the individual patients. Patient-centric means here that the software's primary purpose is to record and view data relating to the individual patient. This type of software may be referred to as electronic medical record (EMR) software, electronic health record (EHR) software, personal health record (PHR) software and other names. Information maintained by the MRS typically includes: patient ID, demographic, info—age, weight, height, Blood Pressure (BP), etc., lab orders and results, test orders and results, medical history, appointment history, appointments scheduled, exam history, prescriptions/medications, symptoms/diagnoses, and insurance/reimbursement info.

CTS includes software for both retrospective and prospective clinical studies. This type of software may be referred to as a Clinical Trial Management System. CTS may also include software for research. CTS is trial-centric which means the primary purpose of the software is to collect and view aggregate data for multiple patients or participants. Although data is collected at the individual patient/participant level, this data is usually viewed "blindly". This means that the viewer and/or analyzer of the data generally do not know the identity of the individual patients/participants. However, data can be viewed at the individual patient/participant level where necessary. This is particularly important where images are involved. CTS typically includes: patient ID, concomitant medications, adverse events, randomization info, data collection, informed consent, aggregated data, and status of study.

In one embodiment, the MRCS 107 of the integrated medical software executed within the client 105 displays medical information 122 of a patient, including, e.g., the medical treatment history of a patient, which may be part of a medical record and/or trial record 120 of the patient. Such records 120 may be downloaded from medical data server 115 in response to a user request. In the case where the integrated medical software integrates MRS, the patient's full identity it typically displayed as part of the medical information. On the other hand, in the case of an integrated CTS, the patient is typically anonymous as discussed above, and the identity of the patient is typically not revealed as part of the displayed medical information.

In one embodiment, image(s) and/or image processing function 121 is integrated with the MRCS. Integration can take the form of the image(s) and/or image processing tools showing up in the same window as the MRCS. Integration can also take the form of a window containing the image(s) and/or image processing tools opening up in a separate window from the MRCS window. It should be noted, however, that in either form of integration, the medical information of the patient and image(s) are displayed within the integrated medical software, without requiring the user of the integrated software to separately obtain the images via another software program.

In one embodiment, image processing tools 123 that are provided by the remote imaging processing server 110 are displayed to the user of the integrated medical software executed on the client 105. In such an embodiment, the available image processing tools 123 are displayed in the integrated medical software as a set of icons or some other graphical representations, which when activated by a user, allow an image to be manipulated by the remote imaging processing server. In one embodiment the image processing software is integrated with the MRCS program and also opens up "in context". "In context" means that the image processing software opens up to show the appropriate image(s) and/or tools for the current user and/or patient and/or affliction. The availability of imaging tools 123 to a particular user depends on the access privileges of that particular user (e.g., doctors vs. medical students). Alternatively, the availability of imaging tools 123 may be determined based on a particular body part of a patient, which may be identified by certain tags such as DICOM tags.

For example, one doctor may prefer that the cardiovascular images for his patients open up in a 3D view, with vessel centerline tools available, yet the abdominal images for his patients open up in a coronal view with the flythrough, or virtual colonoscopy, tools available. He may prefer to have the other views and tools hidden from view. In another example, another doctor may prefer that the images for her patients open up showing the most recent views and tools that she used for that patient. In another example, the default view for cardiovascular cases may be set to show a particular view and tools, but the user may be able to change the default so that his/her preferences override the default views and tools.

In all of the above examples, ideally only the images that relate to the patient being evaluated at that time are able to be viewed. In addition, the user/physician does not need to search to find the images relating to the patient, the images 124 are automatically associated with the correct patient, for example, based on the corresponding patient ID. To do this, the identity of the patient needs to be associated with the patient's images. This can be done by using tags, such as a common identifier, such as an ID number, metadata associated with one or more of the images, mining patient data, body part analysis, or other ways. Also, the appropriate tools need to be shown and inappropriate tools hidden. The tags are discussed in more details below.

For example, an image or image series can be analyzed to determine whether it is a head, abdomen, or other body part, based on the anatomy. A skull has a characteristic shape, as do other parts of the anatomy. A catalog of reference images may be used to help identify specific body parts. Based on this analysis, the appropriate views and/or tools can be made visible to the user, and inappropriate views and/or tools can be hidden. For example, if the image series is of a head/skull, the image series may be shown in a certain view, such as an axial view, and tools associated with the brain visible. In addition, if certain key words, such as "tumor" or "stroke", are found in the MRCS record, specific tools may be shown, such as tools that detect a tumor or evaluate brain perfusion. It is also possible that a patient ID can be determined from the anatomy in an image based on shape, disease, tags etc. for example, an image of a dental area can be matched with dental records to identify a patient from medical images. Or, an identifying tag can be included in the medical image—such as a tag with the patient ID number placed on or near the table of a CT scanner, or on the patient himself.

In another embodiment, the user of the software is able to customize how the image processing software is presented in context. For example, Doctor Y, a cardiologist, may prefer to have the images open up in a 3D model view, and have cardiology tool A and cardiology tool B visible to him. In this example, other views may be hidden (for example, the axial, sagittal, and coronal views) and other tools are hidden (for example, tools relating to the colon or the brain).

Figure 2A:
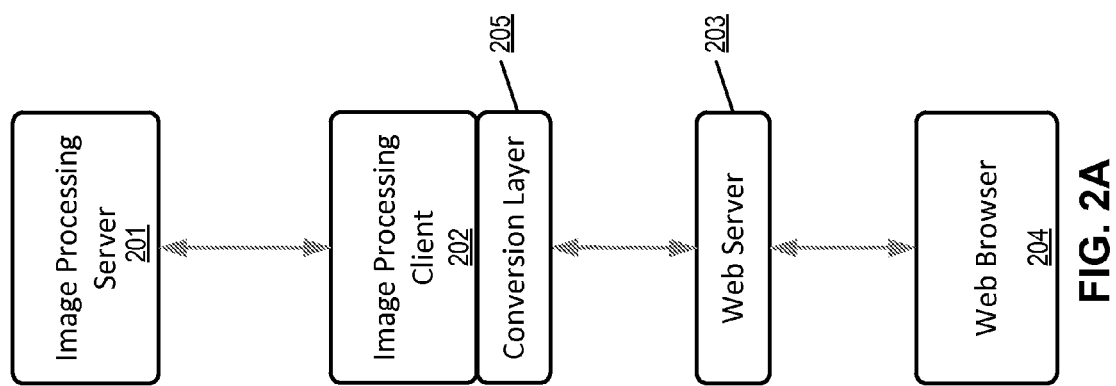
FIGS. 2A and 2B illustrate a web-based architecture of image processing software according to certain embodiments of the invention.

FIG. 2A illustrates a web-based architecture of an image processing software system according to one embodiment. The image processing server 201 performs the heavy work of image processing. The image processing client 202 is a client-server-based client, which resides on a computer, mobile device or other hardware. The conversion layer 205, converts the traditional client information into information that a standard web server 203 can understand. The web server 203 can be a standard web server such as Microsoft IIS (Internet Information Services) server. The server 203 resides on a computer, mobile device or other hardware. Once the image processing information has been translated to a standard web server, any user using any web browser 204 on any computer, mobile device or other hardware can view the images, and use the image processing tools.

Image processing software that employs a web-based architecture is advantageous because it allows the user to access the software via a web browser or other standard web interface. Since many MRCS programs either currently use a web browser interface, or plan to, integrating the graphical user interface (GUI) between two web-based software applications provides the most seamless interface for the user.

A web-based architecture allows superior integration flexibility. Since the web browser can be viewed on any computer, either on the internet or an intranet, the image processing window or frame can be embedded or launched from any MRCS program. The image processing application can further be launched in a standard web browser without any additional plug-in or download, such as FLASH or Java or Citrix. This architecture also allows for significant customization of the image processing interface by user, patient, specialty, etc. This is important for the image processing window to launch in context within the more general MRCS program.

Figure 2B:
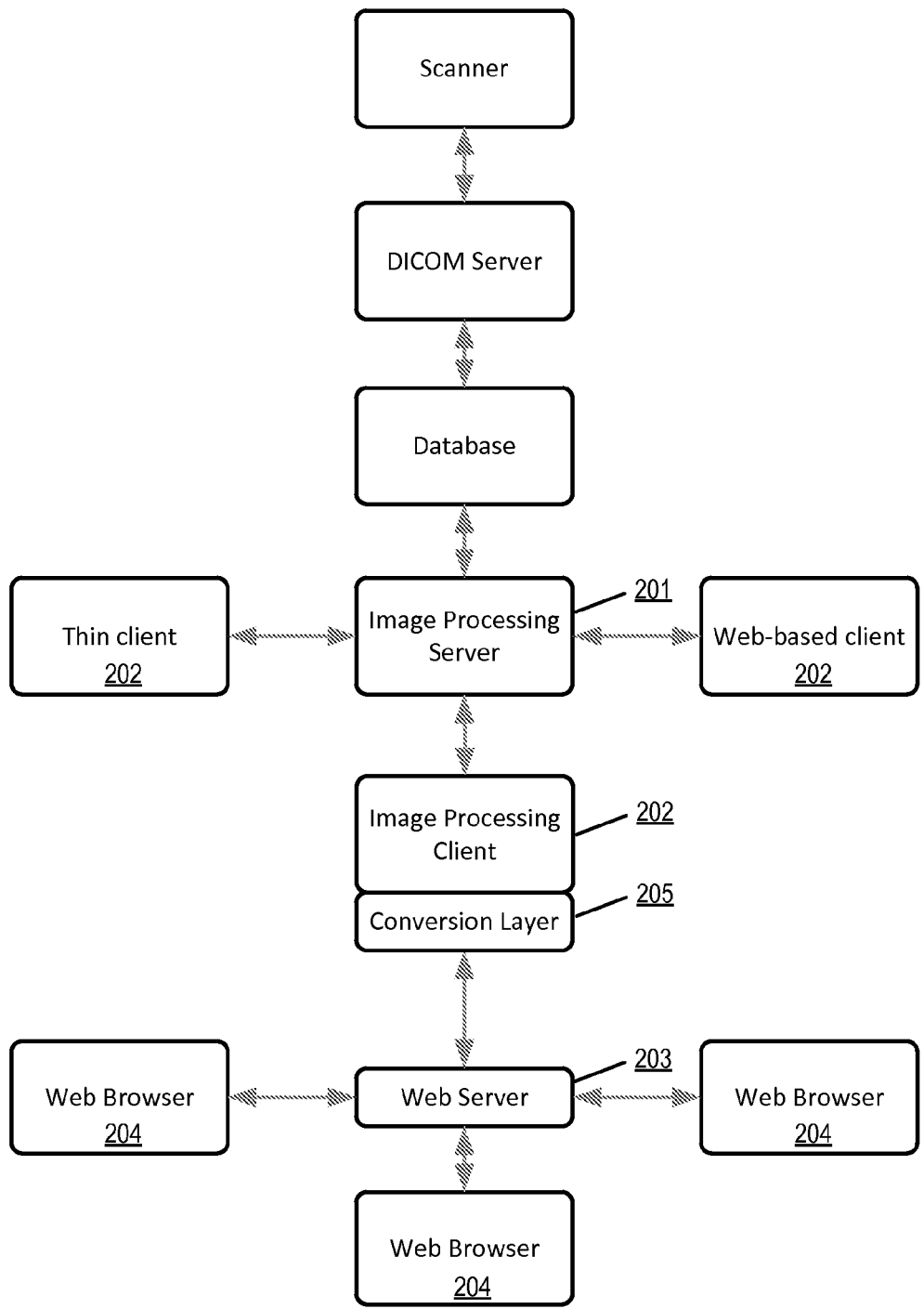

FIG. 2B illustrates a web-based architecture of an image processing software system according to another embodiment. Other client types on other hardware can be launched from the same server, the same data, and even the same session. This allows, for example, for a radiologist sitting at a workstation with client software installed on the workstation to be looking at and manipulating a patient's image(s) while somebody reviewing an EMR via a web browser on another computer is viewing/manipulating the very same images. One user may have a very different interface than another user, but the image processing server can be the same, and the data can be the same. Because the image processing server and/or the conversion layer can control access to tools, images etc., as discussed above, one user may see some tools that the other user may not. One user may see some images or info that the other user may not, dependent upon his access privileges. This could allow a primary physician, for example, to consult with another physician without worrying whether unauthorized images or tools are shown to the consulting physician.

In another embodiment, the image processing software shares quantitative data with the MRCS with which it is integrated. Quantitative data can be extracted from medical images using certain image processing tools. Measurements are taken and tracked. This quantitative data can be associated with the images in the form of meta-data. For example, the RECIST (Response Evaluation Criteria In Solid Tumors) value of a tumor may be measured and tracked over time. This information is important to the user of the MRCS and can be shared with and/or integrated into the MRCS program. For example an EMR may show, in numeric form, the tumor's RECIST values over time, or a clinical trial software program may show the same thing, to help measure outcomes of a particular drug or treatment. Another example is the integration of quantitative image data with medical dictation software, such as Nuance POWERSCRIBE® 360. The data associated with the image(s) can be presented within the dictation software allowing the user to dictate around the data. For example, if the RECIST value of a tumor is 11 mm, the dictation software can be prepopulated with this information, then the physician only needs to add dictation such as "the tumor RECIST value is . . . ".

The quantitative data can be shared in the other direction also. The MRCS may contain data which is relevant to the images. For example, a patient's weight or BMI may be pulled into the imaging software and displayed along with the images or used in quantitative image calculations. This same type of quantitative integration can be done with MRCS packages also, including EMR software. Quantitative data, or other metadata, can be exchanged between the MRCS and the medical imaging software via XML or other languages. Where established protocols exist, these can be used to share the quantitative data between software packages. For example, the AIM (annotation and image markup) protocol may be used.

Where appropriate, a user of the MRCS can give access to another user, such as in the case of a referral. In this case the referring user may want to give access to only a portion of the MRCS, such as access to a particular patient or access to only partial data of a patient. The referring user may want to include quantitative data in the accessible data. In this case, the referring user would be able to give access to not only the quantitative data, but also the images from which the quantitative data came, if the data came from images. This would give context to the quantitative data. For example, if the quantitative data were measurements of a tumor size, both the referring and the referred user would be able to access images of the tumor from which the measurement was taken. If the tumor has been tracked over time, the users would be able to access images for each quantitative measurement.

Figure 3:
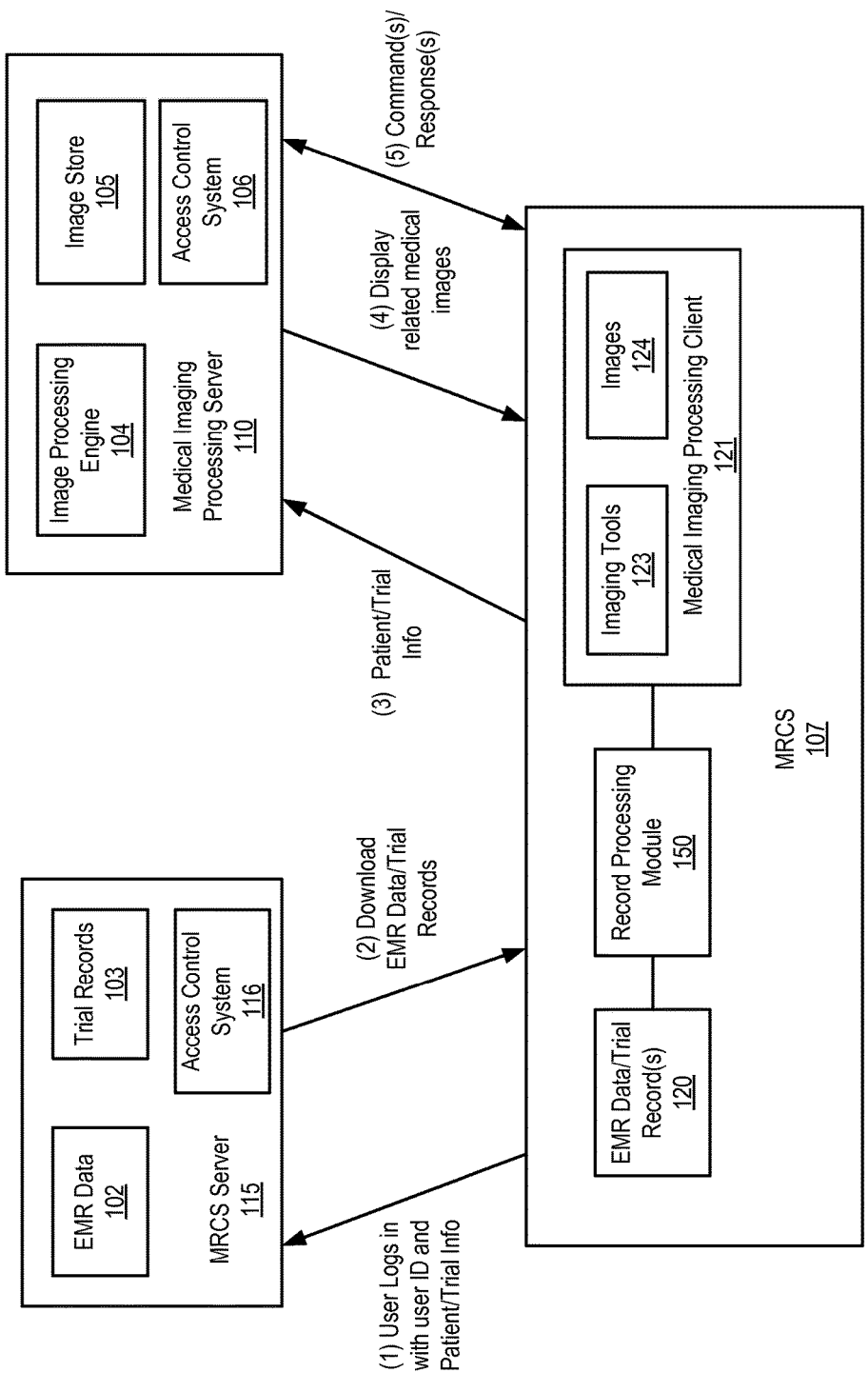
FIG. 3 illustrates the communication scheme between the servers and client of the integrated medical software system according to one embodiment of the invention.

FIG. 3 illustrates the communication between an integrated client and a medical imaging processing server and a medical data server according to one embodiment. Referring to FIG. 3, at step (1), a user (e.g., a physician) executing the integrated medical software on client 105 logs onto the remote medical data server 115. In one embodiment, the login credentials include a user ID and password. Upon completion of the login process, the user provides the medical data server 115 with the information pertaining to the record that he or she wishes to view. For example, if the user intends to view the EMR of a patient, the user would provide information pertaining to the patient. In one embodiment, the patient information includes the patient ID. On the other hand, if the user intends to view clinical trial records, the user would provide the medical data server 115 with clinical trial information.

Upon receiving the necessary information from the user via the client 105, at step (2), the medical record (e.g., EMR) or clinical trial record is viewed from the medical data server 115 to the client 105, which is displayed within the integrated medical software GUI. In one embodiment, the GUI is the same window as the integrated medical software window. In an alternate embodiment, the GUI is a separate window from the integrated medical software window.

In one embodiment, a user may wish to view image(s) and/or edit images associated with the viewed medical record or clinical trial record. In such an embodiment, the user of the integrated medical software executes step (3) by accessing the remote medical imaging processing server 110. Upon successfully being authenticated by the remote medical imaging processing server 110, the user would provide the server with information pertaining to the images that he or she chooses to view. For instance, if the user chooses to view images associated with a particular EMR record, the MRCS would provide the medical imaging processing server 110 with information pertaining to the patient. In one embodiment, the information includes the patient ID and/or medical treatment. On the other hand, if the user chooses to view images associated with a clinical trial record, the MRCS would provide the medical imaging processing server 110 with information pertaining to the clinical trial and/or patient. In one embodiment, the medical information transmitted to the remote medical imaging processing server 110 includes a body part identifier, which identifies a body part of the patient. According to one embodiment, the patient/trial information identifying the images may include certain tags such as DICOM tags. The above process is automatically processed without requiring the user to specifically provide such information. The images may be identified by the image processing server based on tags that are obtained from the EMR data or trial records, where the tags may be automatically extracted from the EMR data or trial records and transmitted to the remote medical image processing server when the user initiates the access to the medical image processing server. In one embodiment, the authentication process may be synchronized between access control system 116 and access control system 106, such that once the user has been successfully authenticated by one, i.e., access control system 116, the user is also automatically authenticated by the other, i.e., access control system 106. Alternatively, MRCS 107 may cache the login credentials (e.g., usernames and passwords) locally and when the user access either of systems 115 and 110, MRCS 107 may automatically log into the systems without having to prompt the user for the same.

According to one embodiment, certain detailed information of a medical record of patient, some of the information may be associated with different tags. For example, a tag may identify a body part of a particular medical treatment of a patient, where the medical treatment may also be identified by another tag. When the user wishes to obtain a medical image that is associated with that particular medical record, the user can simply activate a control to access medical imaging processing server 110 to request the related images. The request transmitted to medical imaging processing server 110 may automatically include at least some of the tags. In response, server 110 can identify the specific images that are associated with the particular portion of the medical record at the point in time based on the tags. Only those specific images are then displayed by the server 110 within medical SW 107 along with the medical record in question. Further, a set of imaging processing tools is identified by server 110 and the corresponding icons are displayed to allow the user to utilize the tools for manipulating the images. The availability of the tools may be determined based on the tags, as well as the access privileges of the user.

Referring to back to FIG. 3, upon receiving all the necessary information from the client 105, at step (4), images associated with the information provided by the user are displayed by medical imaging processing server 110 to the client 105. In one embodiment, the image(s) to be viewed are identified by the remote medical image processing server 110 based on the patient ID and/or optional medical treatment history of the patient, which may be represented by tags. In one embodiment, the images to be displayed are identified by the body part identifier provided by the MRCS as part of step (3) discussed above. Once the images are displayed to the client 105, the user may view them through a graphical user interface (GUI) that is included in the integrated medical software. Note that throughout this application, an image displayed by medical image processing server 110 represents a particular view of a medical image stored in and rendered by medical image processing server 110, in response to a rendering command or request. The displayed version of the image may or may not have a different resolution compared to the original image maintained by medical image processing server 110. In one embodiment, the GUI is the same window as the integrated medical software window. In an alternate embodiment, the GUI is a separate window from the integrated medical software window. In one embodiment, the displayed image(s) and the medical information of the patient are displayed within the integrated medical software without requiring the user of the integrated software to separately obtain the image(s) via another software program. Conventional systems require EMR software to obtain patient information and separate image processing client software to obtain medical images from a medical image processing server. In this situation, the conventional systems require the user to at least manually enter the patient information from the EMR software to the image processing client in order to obtain the associated medical images. Embodiments of the present invention would automatically obtain the associated medical images without user intervention, for example, based on tags (see FIG. 6 for examples of tags).

In one embodiment, the user may manipulate the images (e.g., zooming in/out), or view the images in different angles/modes, etc. In such an embodiment, step (5) may be executed by the user activating one of the icons representing the imaging tools that are displayed on the GUI of the integrated medical software, which causes the client 105 to send relevant commands to the remote medical imaging processing server 110. In response to the commands, the remote medical imaging processing server 110 renders the images to meet the requested view parameters and transmits responses back to the client 105, which causes the images to be displayed in the desired mode. It will be appreciated that step (5) may be executed repeatedly as a typical user would manipulate the images numerous times, and/or wishes to view the images in several different modes.

Figure 4A:
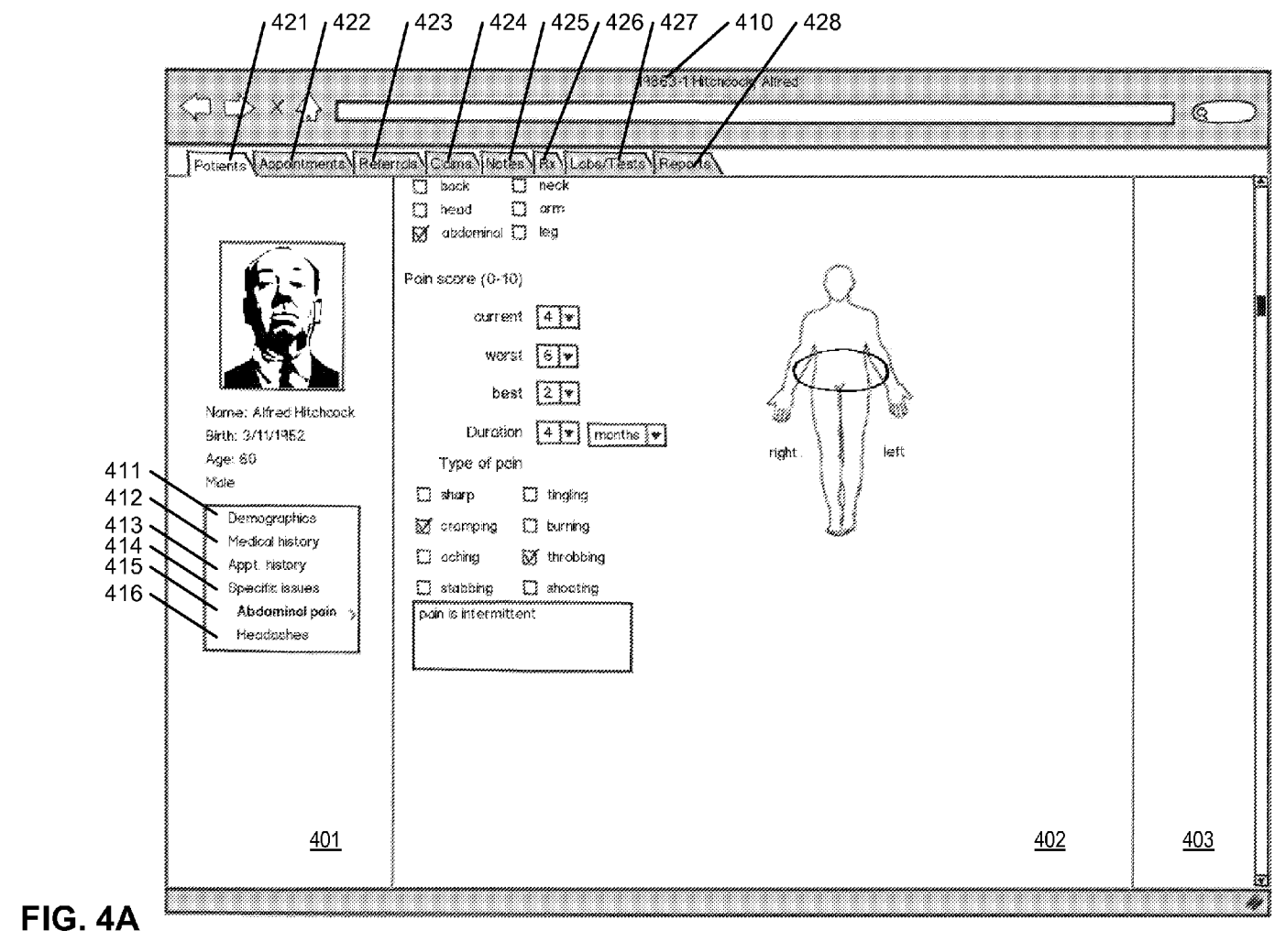
Figure 4B:
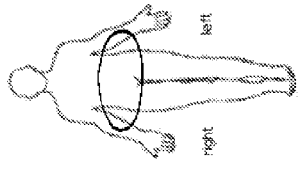

FIGS. 4A-4G are screenshots illustrating a graphical user interface of an MRS according certain embodiments. Referring to FIG. 4A, the information displayed is related to a particular patient Alfred, who is identified by a patient ID 410 (e.g., 19863-1). The GUI includes a variety of pages such as patient information page 421 having display areas 401-403. Alfred's demographic data can be accessed by selecting from the "Demographics" link 411 in the menu displayed in display area 401. Similarly, Alfred's medical history can be accessed by clicking on the "Medical history" link 412 in the menu 401. Alfred's appointment history can be accessed via link 413. Across the top of the screen, the user can access Alfred's full appointment data (history and upcoming) 422, any Dr. referrals 423, insurance information 424, any patient notes 425, prescription information 426, laboratory and testing information 427, and any reports 428 available for Alfred. Also on the menu 401 is a listing of Alfred's specific issues 414, including, in this example, abdominal pain 415 and headaches 416. When the user clicks on abdominal pain 415, the display area 402 of the screen shows information specific to abdominal pain, including symptoms and possibly a diagnosis. This screen is only a representation, other layouts and features may also be present and/or absent.

Referring now to FIG. 4B, there are several tabs across the top which may include, for example, appointments, referrals, insurance claims, notes, prescription drugs (Rx), labs/tests, and reports, similar to the GUI as shown in FIG. 4A. The display area 401 of the GUI shows certain detailed medical information 404 of the patient, such as name and age of the patient, as well as a menu which may show things like appointment history and specific medical issues. In this particular FIG. 4B, the issue, "abdominal pain" has been selected and more details of the abdominal pain are shown in display area 402 of the GUI. Note that image thumbnails are displayed in display area 403 to show abdominal related images or image series. As previously stated, these images are showing up automatically in a contextual manner—note that they are only images relating to this patient's abdominal pain (e.g., based on a tag associated with the abdominal pain), not images relating to his headaches or other images, for example, based on the selective medical information 404. They are also only images that relate to this patient (e.g., based on the patient ID or patient ID tag). In this and other examples, the image thumbnails may be in a browser frame within the EMR browser frame. These related images may be identified, and associated, via tags and/or patient ID, etc.

Figure 4C:
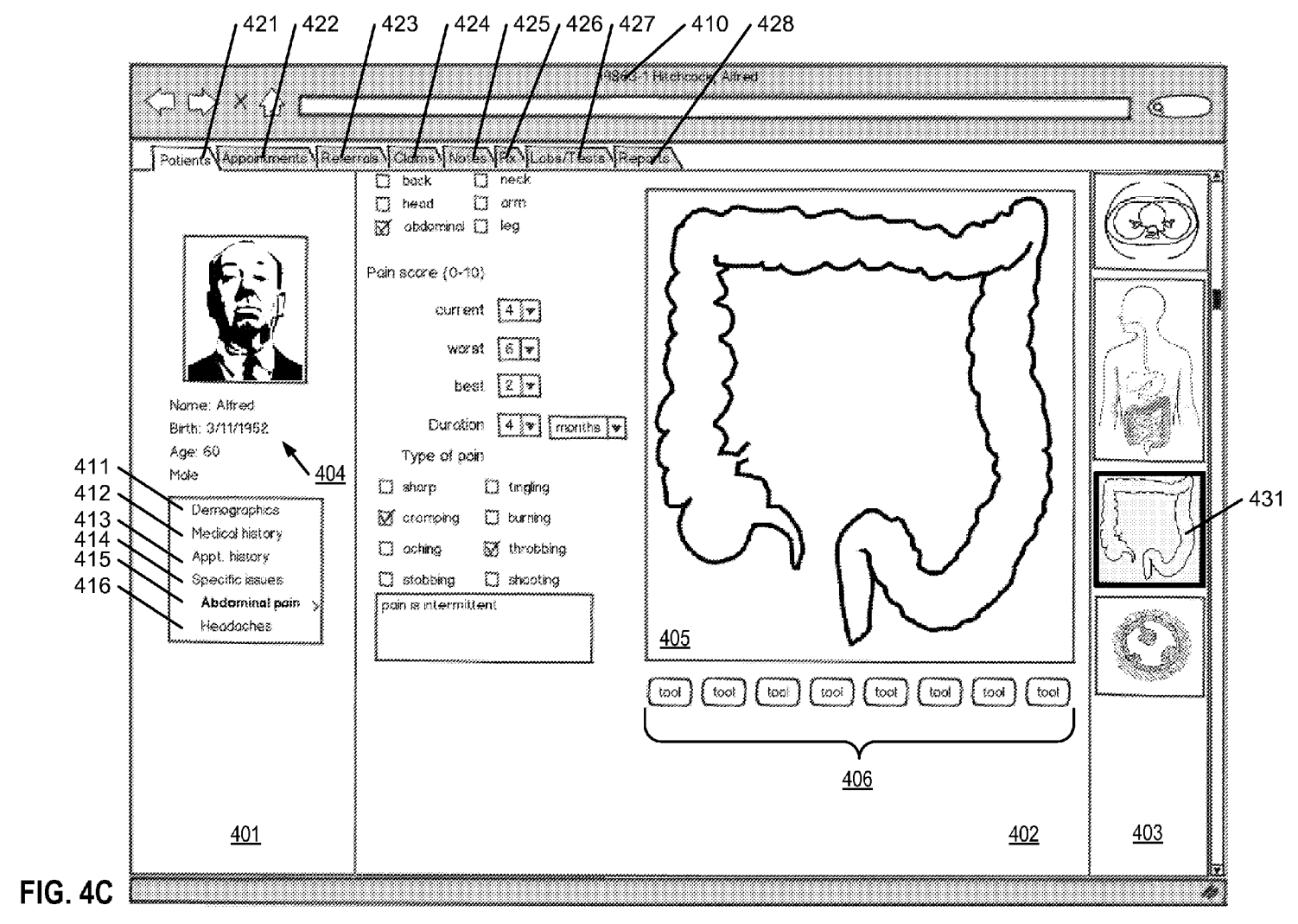

Referring now to FIG. 4C, it is assumed the third thumbnail 431 from the top (e.g., highlighted image from display area 403), the image of the colon, was clicked. In response to such an action, a larger version of the selected image(s) is displayed in display area 405, which may be displayed within the same window as, or a separate window than, the GUI. In addition, a set of icons 406 representing a set of imaging rendering tools are also displayed. The availability of icons 406 may be different for different users and/or for different images (e.g., based on different medical information). These tool buttons could be tools to manipulate the image(s) of the colon. For example, a tool button might enable the user to do a fly-through through the colon, or to locate suspected polyps within the colon. Note that although only a still image is shown in these figures, the images may represent a series of scan slices, such as slices from a CT scan. There could be hundreds or even thousands of slices represented in an "image". Because of this, the tools that can be used to process the image may be quite advanced. The image can be viewed as a 3D model and rotated, manipulated etc. The images may be dynamic, or moving, as in a cine or movie. A possible list of tools is included later in this document. In FIG. 4C, note that the tools that are visible may be tools that only relate to the colon, or to the abdomen, or to this particular user.

Figure 4D:
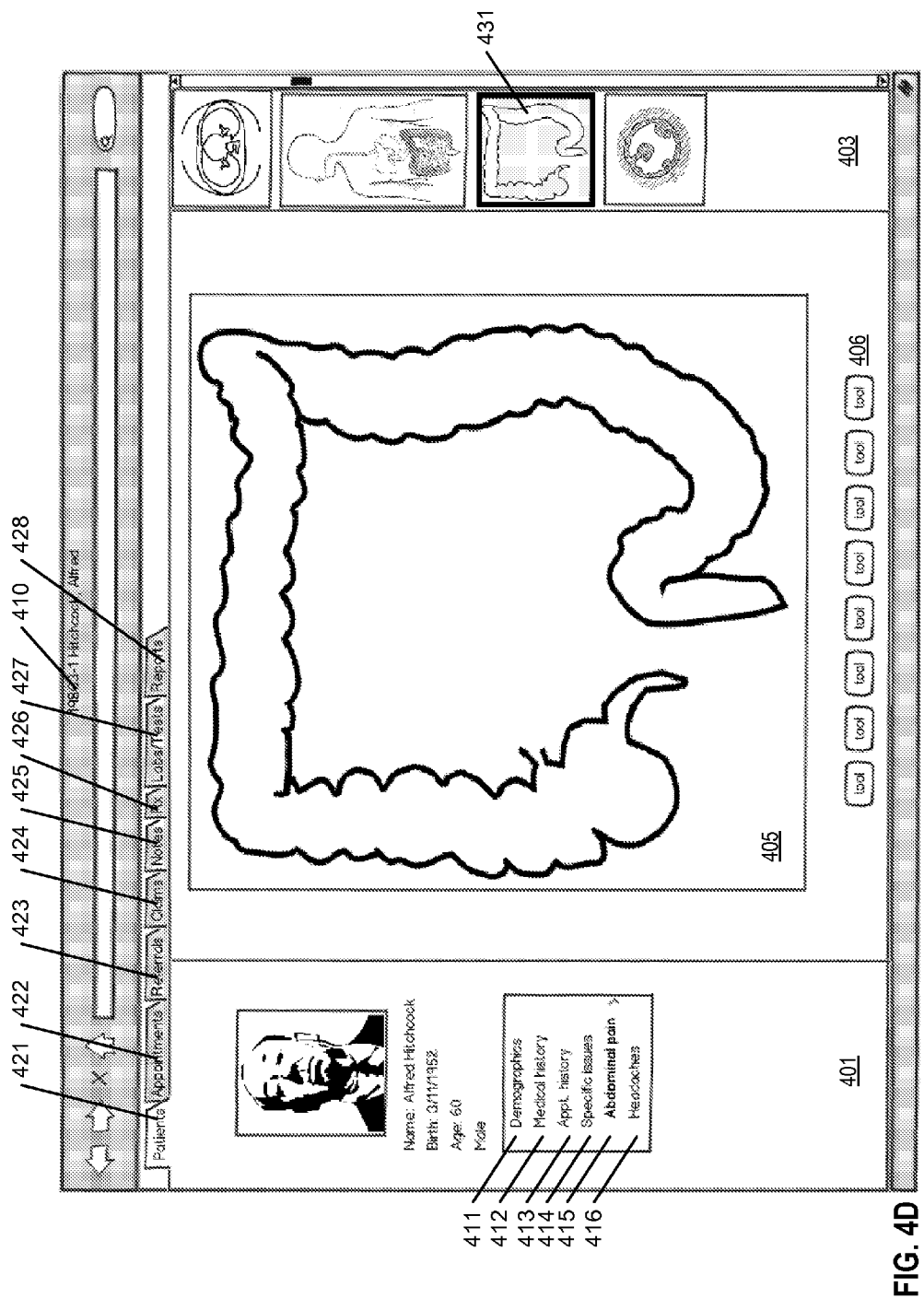

FIG. 4D illustrates another example of what could happen when the user clicks on one or more of the image thumbnails. In this example, the third thumbnail 431 from the top, the image of the colon, was clicked. As a result, a window showing a larger version of the image(s), and tool buttons, opens within the EMR screen. This is similar to the example in FIG. 4C except that the window for the larger image(s) and tools is larger.

Figure 4E:
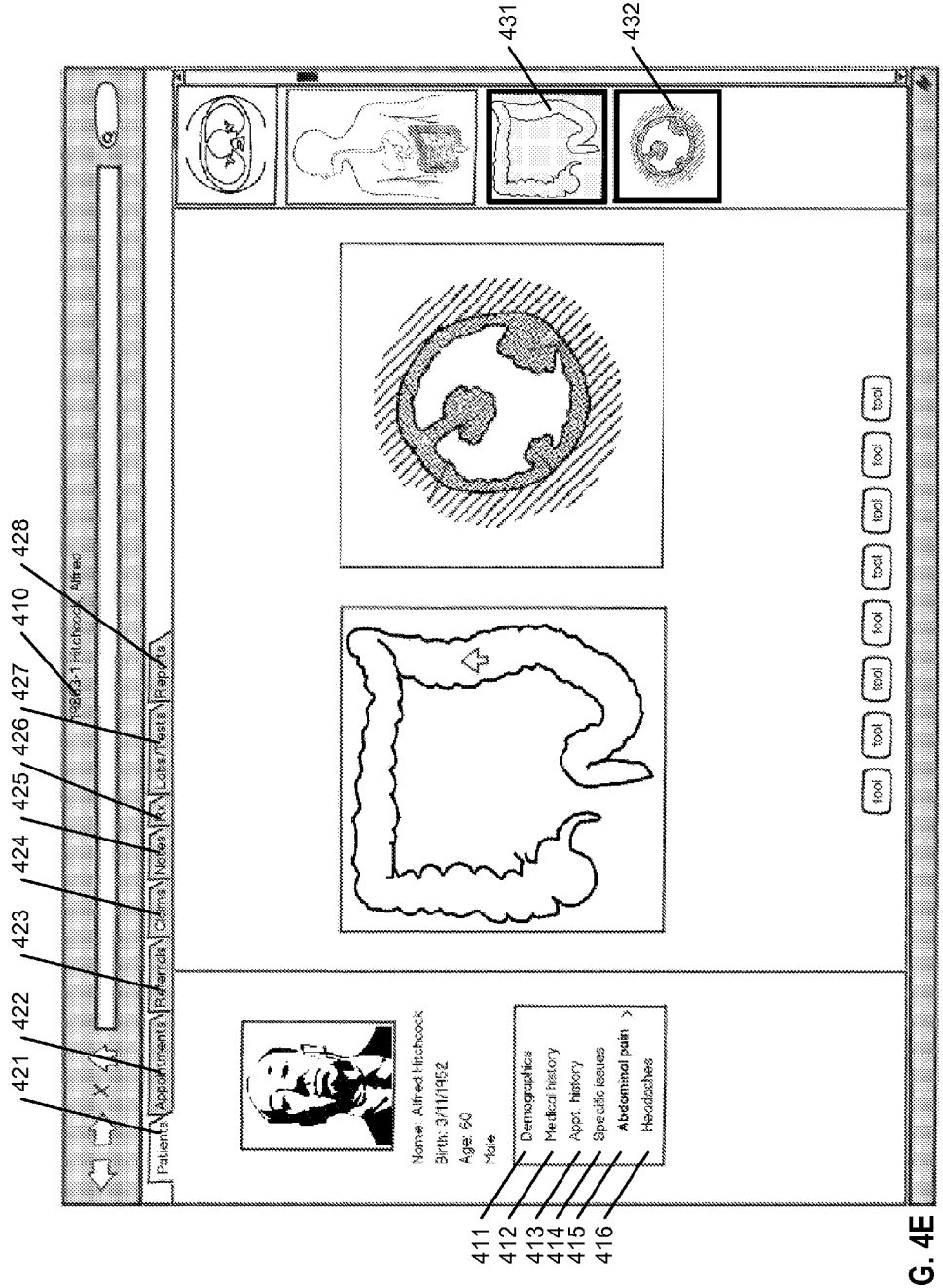

FIG. 4E illustrates another example of what could happen when the user clicks on one or more of the image thumbnails. In this example, the third thumbnail 431 from the top was clicked and the fourth image 432 from the top was clicked. As a result, a window showing a larger version of both of the images and tool buttons opens within the EMR screen. The two images can be compared and/or viewed together. The two images may be registered to each other so that as the user manipulates one of the images, the other image is affected appropriately. For example, in FIG. 4E, the right image represents a colon fly-through, where the user sees the inside of the colon as if he/she were flying through it. The left image shows an arrow depicting where in the colon the user is "flying".

Figure 4F:
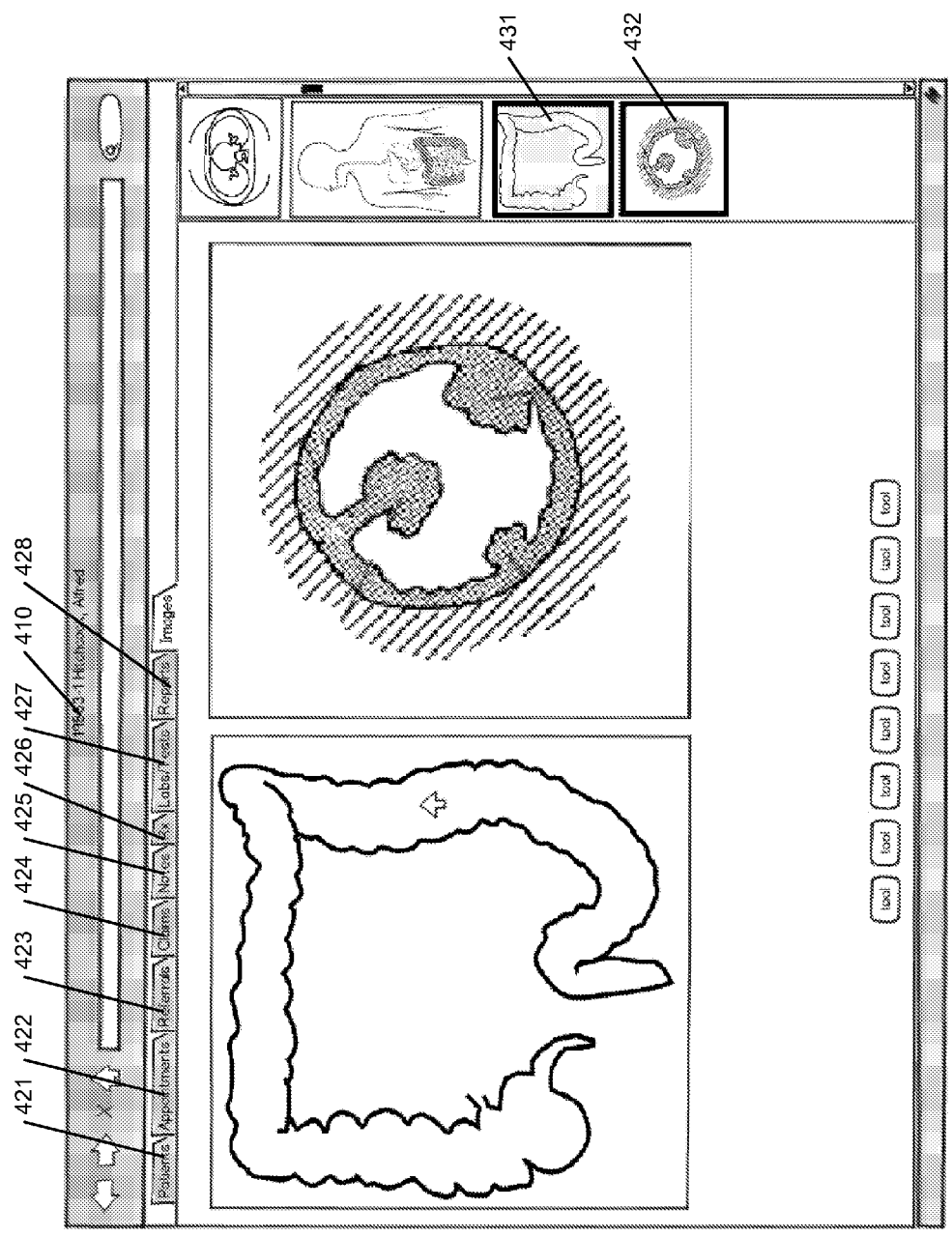

FIG. 4F illustrates another example of what could happen when the user clicks on one or more of the image thumbnails. In this example, the third thumbnail from the top was clicked and the fourth image from the top was clicked. As a result, a window showing a larger version of both of the images and tool buttons opens in a new tab within the EMR screen. This example is similar to that depicted in FIG. 4E except that there is more screen area available to the image viewing/processing. Note that the user can easily navigate among the top tab buttons if he/she wants to view different information concerning this patient.

Figure 4G:
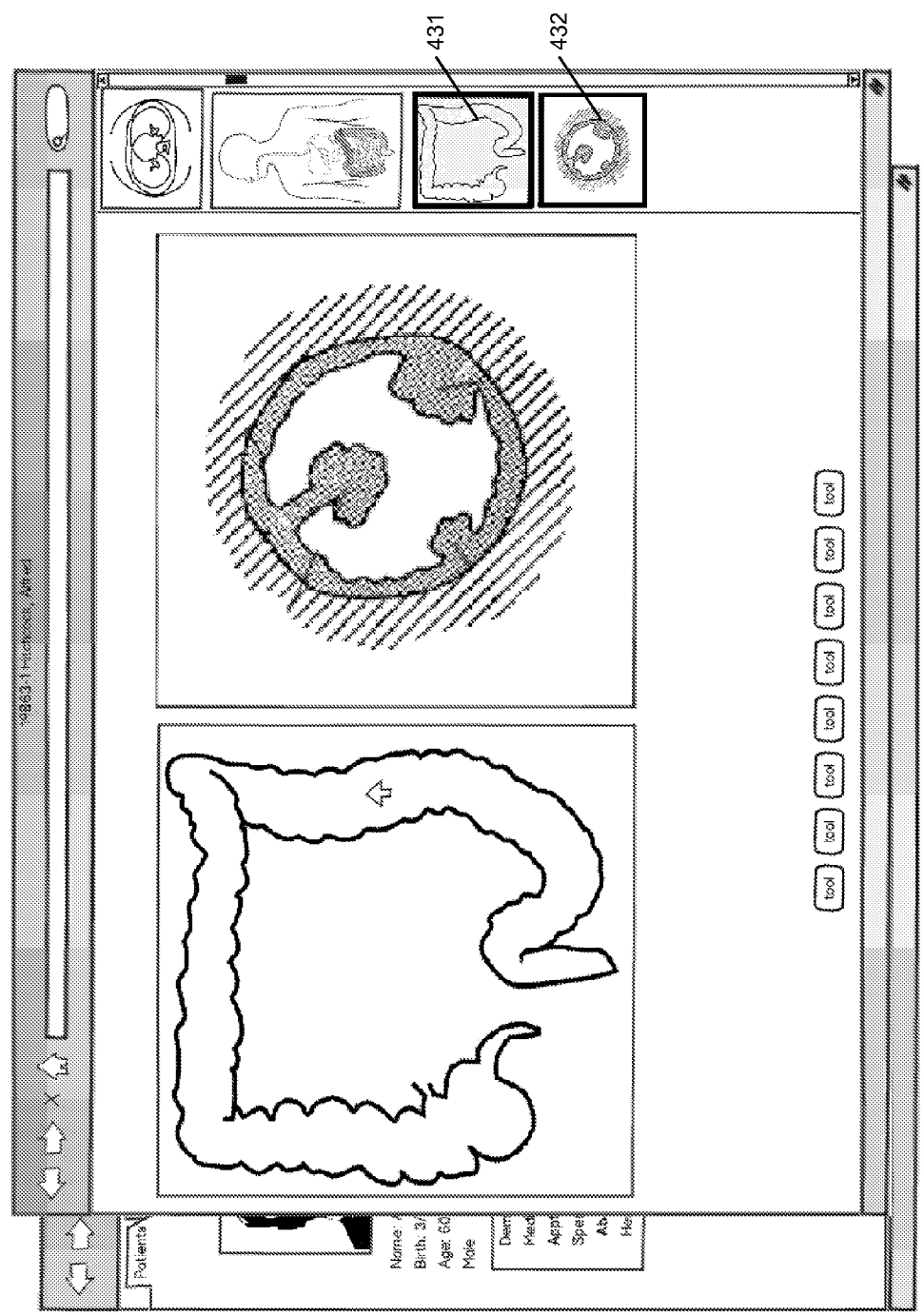

FIG. 4G illustrates another example of what could happen when the user clicks on one or more of the image thumbnails. In this example, the third thumbnail from the top was clicked and the fourth image from the top was clicked. As a result, a new window showing a larger version of both of the images and tool buttons opens. These screen configurations can be achieved using browser frames or other ways. These, and other, image viewing and processing windows can be opened or launched in other ways also. The thumbnails may or may not be visible. The images could be launched via a simple "images" button or link, or could automatically launch where appropriate images exist.

Figure 5A:
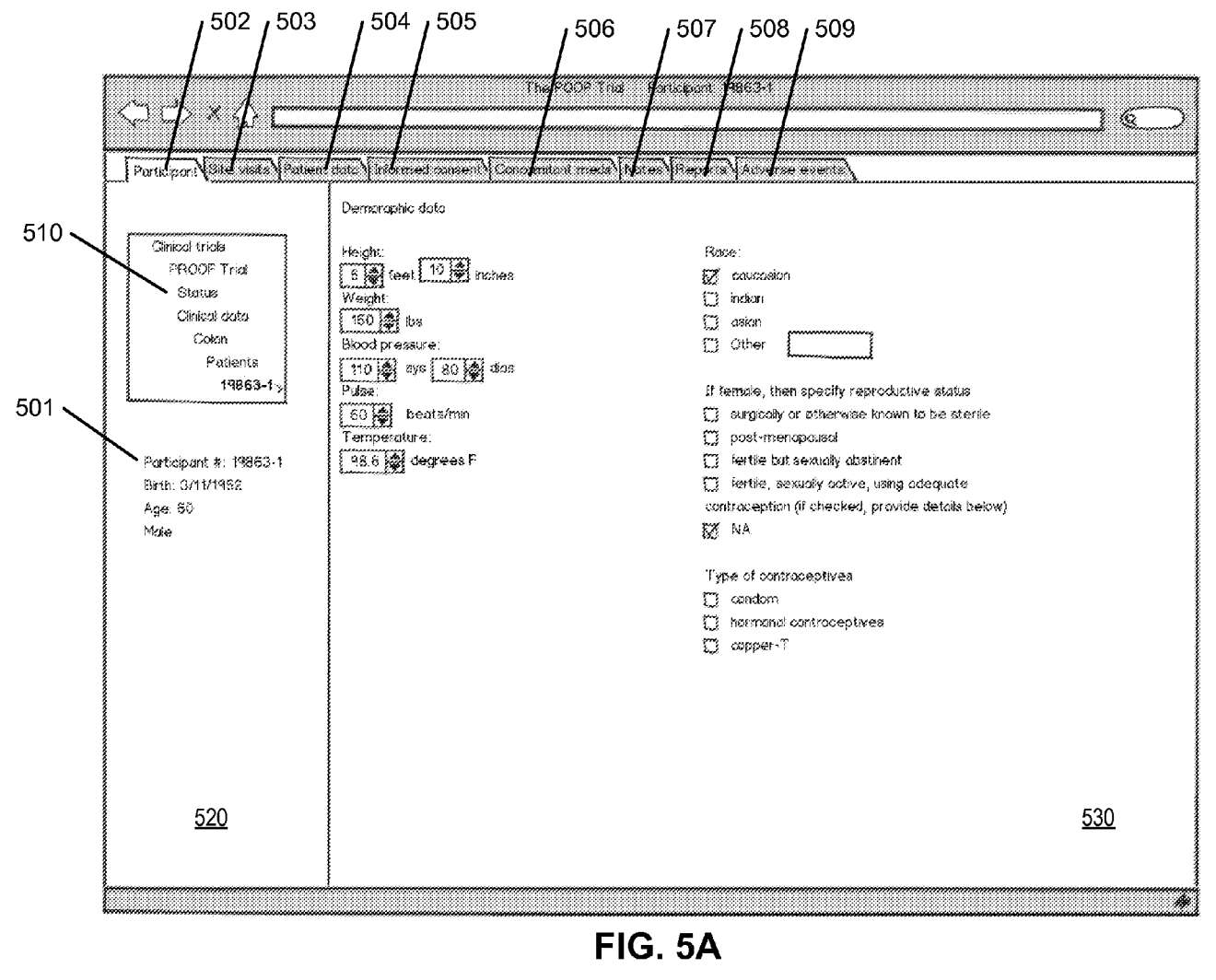
Figure 5B:
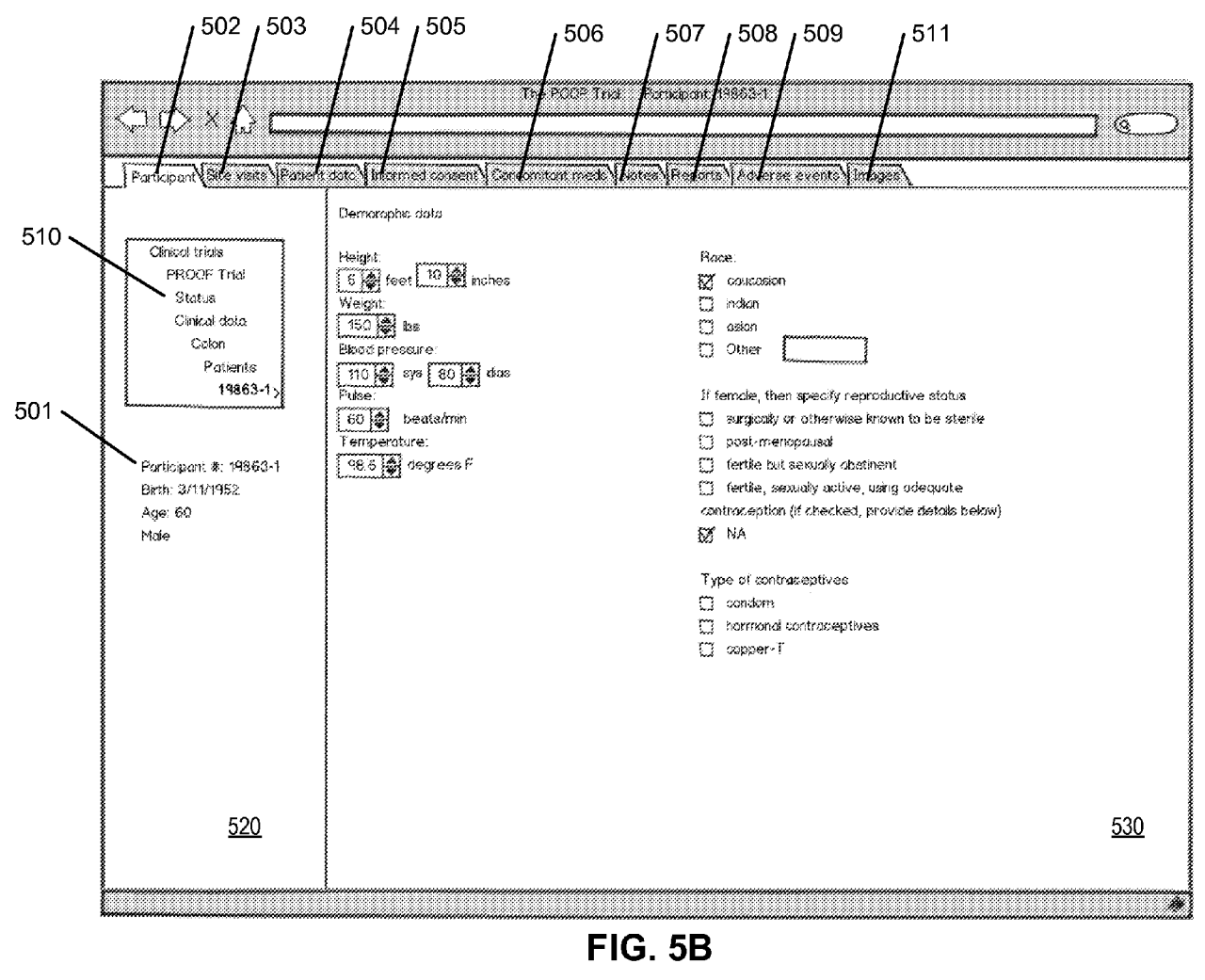
Figure 5C:
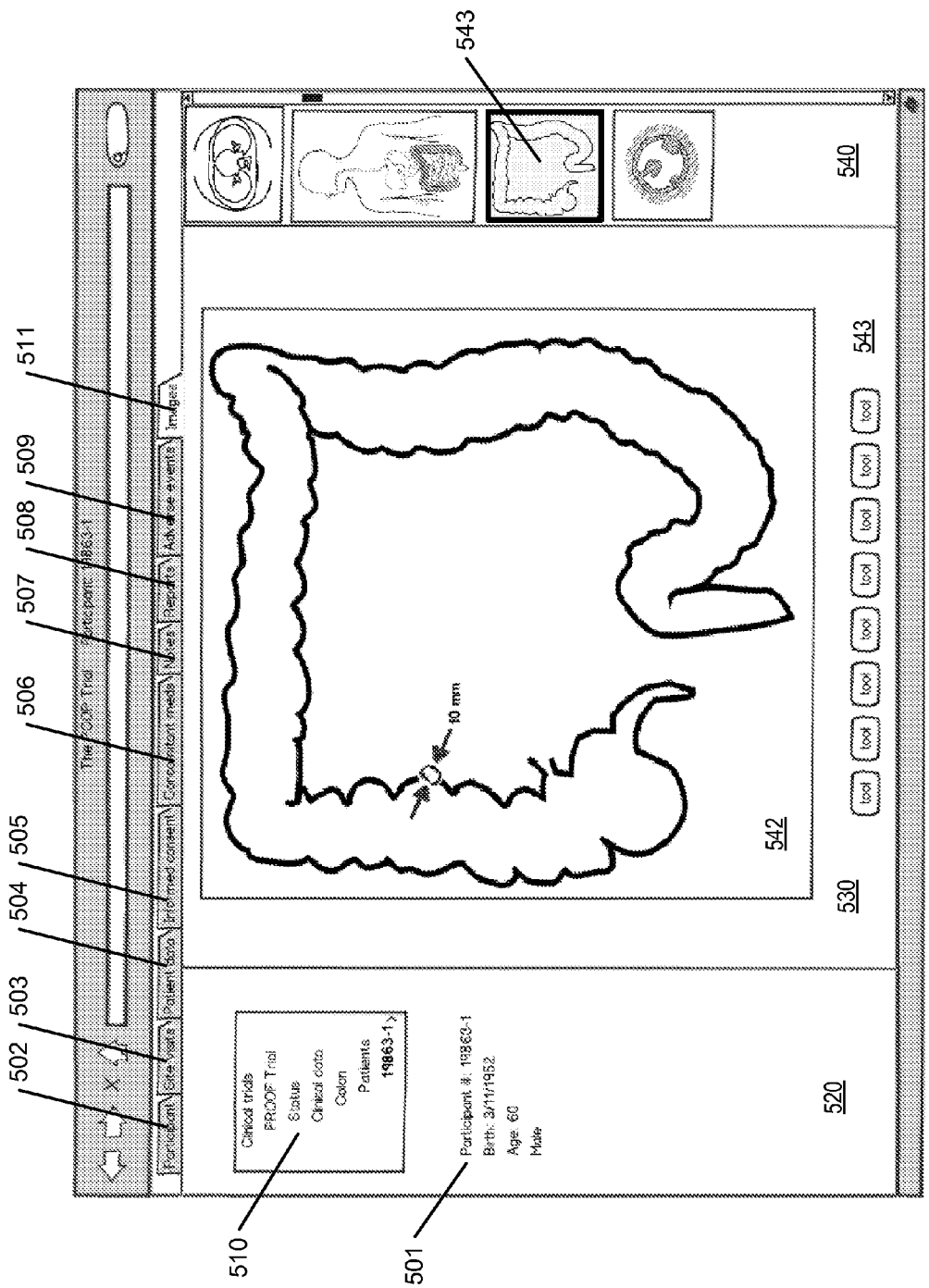

The integration can also be implemented between image processing software and any type of MRCS. For example, images can be integrated with clinical trial software, CTS. FIGS. 5A-5D are screenshots illustrating a GUI of integrated CTS according to certain embodiments of the invention. Referring to FIG. 5A, this screenshot is specific to a clinical trial named PROOF. The user can drill down within the trial to access data relating to one of the patients/participants in the trial via participant page 502. Here the patient is only referred to by patient ID 501, without displaying the patient's name. Across the top of the screen, the user can access information relating to specific site visits 503, patient data 504 which has been collected, the patient's informed consent 505, any concomitant medication 506 the patient may be taking, any notes 507 or reports 508, and any adverse events 509 that the patient may have experienced during the trial. If the user clicks on the status link 510 on the left menu 520, study status info, including aggregate data info would be available and can be displayed in display area 530. In addition, features such as randomization may be configurable via separate screens, or may simply occur behind the scenes within the software.

FIG. 5B illustrates an example of a screen from clinical trial software for an anonymous participant in which images are integrated. There are several tabs across the top which may include, for example, participant 502, site visits 503, patient data 504, informed consent 505, concomitant medications 506, notes 507, reports 508, adverse events 509, and images 511 etc. The left side of the screen shows some basic demographic information, such as the age and sex of the participant. In this particular figure, the clinical trial, "PROOF" has been selected and more details of this participant in this clinical trial are shown in the middle of the screen.

FIG. 5C illustrates what happens when the images tab 511 is clicked. Note that the image thumbnails to display area 540 of the screen also show images or image series that relate to this participant and this clinical trial. In this example, the third thumbnail 541 from the top, the image of the colon, was clicked. As a result, a window showing a larger version of the image(s) 542, and tools buttons 543, opens within the clinical trials software screen. This could be in a frame of the browser or embedded in some other way. Also note that some tool buttons are now available. These tool buttons 543 could be tools to manipulate the image(s) of the colon. For example, a tool button might enable the user to do a fly-through through the colon, or to locate suspected polyps within the colon. Note that although only a still image is shown in these figures, the images may represent a series of scan slices, such as slices from a CT scan. There could be hundreds or even thousands of slices represented in an "image". Because of this, the tools that can be used to process the image may be quite advanced. The image can be viewed as a 3D model and rotated, manipulated etc. A possible list of tools is included toward the end of this document. Note that the tools 543 that are visible may be tools that only relate to the colon, or to the abdomen, or to this clinical trial, or to this particular user. In this example, a polyp detection and measurement tool has been used, and the resulting information is displayed on the screen. The image shows the location and size of the polyp within the colon. The information relating to this detection and measurement is usually stored with the image in the image metadata.

Figure 5D:
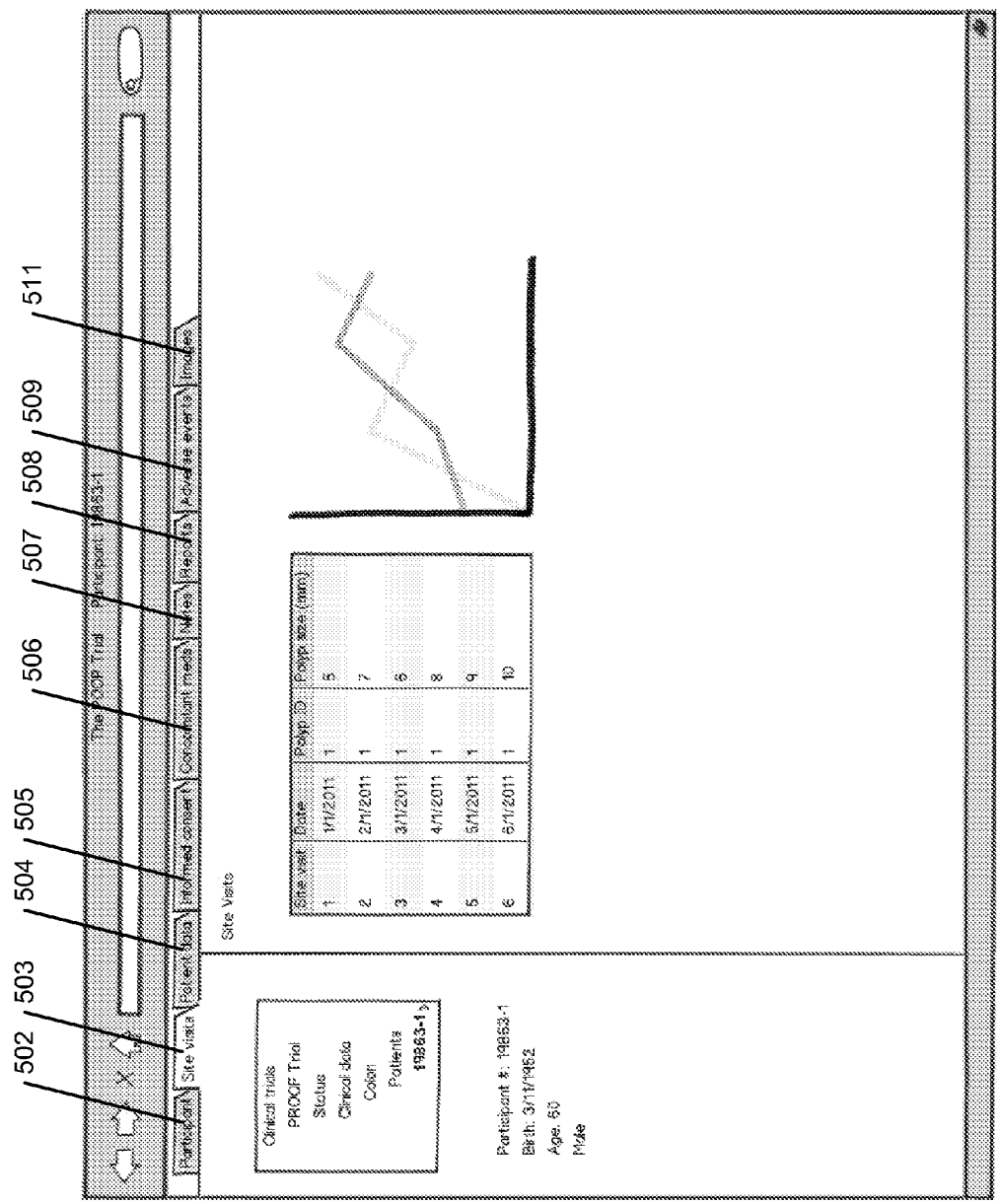

FIG. 5D illustrates how the quantitative information stored in the image metadata can be integrated with the clinical trial software. In this example, the diameter of a particular polyp has been tracked over time and stored in the image metadata. This quantitative information has been integrated with the clinical trial software so that it shows up in the table under the site visits tab. The data can also be represented in a graph or in other ways. The integration of image(s) and/or image processing with MRCS exists on three levels. The first level of integration involves making sure the right image(s) are displayed in the right context, e.g., patient, body part, modality, etc. The second level of integration involves making sure the right tools are displayed for the image(s), e.g., relevant tools are displayed according to the workflow, preferences, etc. The third level of integration involves making sure the right preference(s) are used within the tools, workflow, etc. In one embodiment, integration of image(s) and/or image processing with MRCS is achieved by use of tags.

Figure 6:
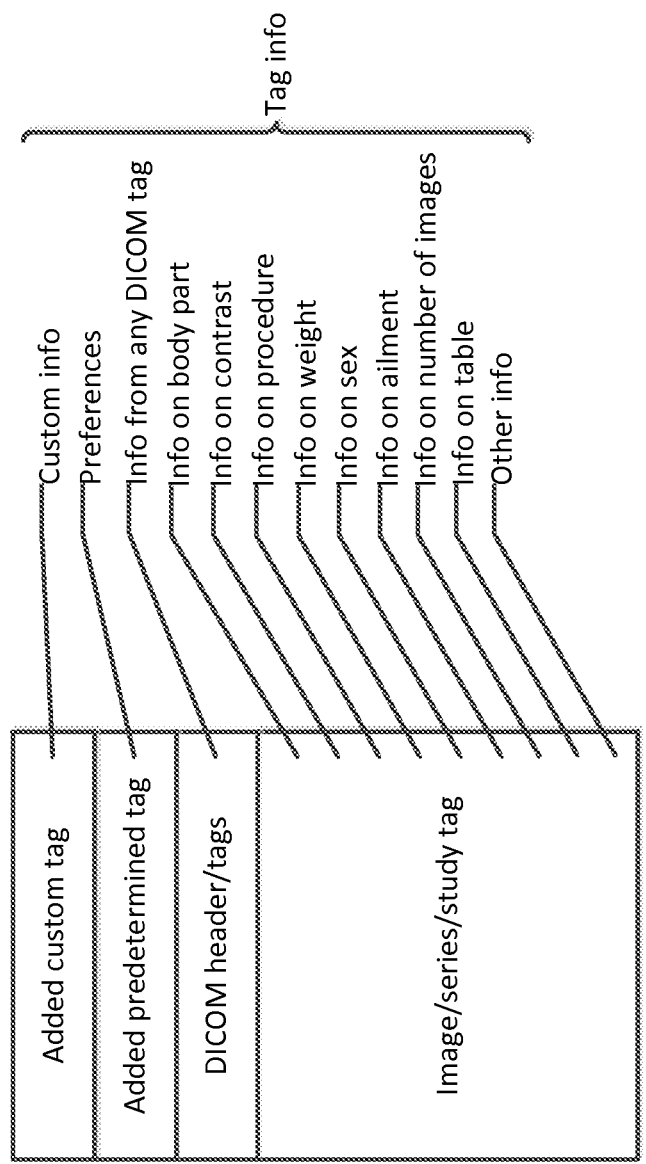
FIG. 6 illustrates the types of tags that may be associated with images, and used by the MRCS to open up the correct image(s) and tool(s).

FIG. 6 illustrates the types of tags that may be associated with images, and used by the MRCS to open up the correct image(s) and tool(s). The DICOM standard includes several tags associated with image data. A partial list of tags is included in the DICOM standard published by the National Electrical Manufacturers Association. For example, there are DICOM tags relating to modality, patient name, patient ID, body part examined, requesting physician, etc. Custom, or private, DICOM tags can also be created and become part of the DICOM header. These tags can be used to integrate imaging software with any MRCS. As described above, at least some of the tags may be utilized to specify or identify certain images stored in the image processing server. Some of the popular DICOM tags are listed as follows:

| Tag Name | Tag ID | Description |
| --- | --- | --- |
| SOPInstanceUID | -80018 | Uniquely identifies the SOP Instance. |
| StudyDate | -80020 | Date the Study started. |
| AcquisitionDate | -80022 | The date the acquisition of data that resulted in this image started |
| StudyTime | -80030 | Time the Study started. |
| Modality | -80060 | Type of equipment that originally acquired the data used to create the images in this Series. |
| Manufacturer | -80070 | Manufacturer of the equipment that produced the composite instances. |
| InstitutionName | -80080 | Institution where the equipment that produced the composite instances is located. |
| InstitutionAddress | -80081 | Mailing address of the institution where the equipment that produced the composite instances is located. |
| StationName | -81010 | User defined name identifying the machine that produced the composite instances. |
| StudyDescription | -81030 | Institution-generated description or classification of the Study (component) performed. |
| SeriesDescription | (0008,103e) | User provided description of the Series |
| ManufacturersModelName | -81090 | Manufacturer's model name of the equipment that produced the composite instances. |
| PatientSex | -100040 | Sex of the named patient. Enumerated Values: M = male F = female O = other |
| PatientAge | -101010 | Age of the Patient. |
| PatientSize | -101020 | Length or size of the Patient, in meters. |
| PatientWeight | -101030 | Weight of the Patient, in kilograms. |
| BodyPartExamined | -180015 | Text description of the part of the body examined. |
| DataCollectionDiameter | -180090 | The diameter in mm of the region over which data were collected |
| StudyInstanceUID | (0020,000d) | Unique identifier for the Study |
| SeriesInstanceUID | (0020,000e) | Unique identifier of a Series that is part of this Study. |
| SeriesNumber | -200011 | A number that identifies this Series. |
| InstanceNumber | -200013 | A number that identifies this image. |

Additional tags can be set up to be associated with image data. For example, these can be preset tags that are regularly used, such as which tools are associated with the image data. These tags can be changed depending on the situation. For example, some physicians may prefer different tools associated with a certain type of image. These tags could also include what workflow is associated with image data.

Custom tags can also be associated with image data. For example, a physician may want to set up the associations for their own studies. In this way, the physician can be assured that image data is properly associated with the correct patient, body part, modality etc. In one embodiment, custom tags can be associated with image data as follows: when an image series or study is first opened, the user may want to attach a tag to it. The tag may be at the individual image level, image series level or at the study level. This tag will allow the image/study/series to be associated automatically going forward. The label may indicate the patient, the body part, the procedure type, the modality, the study center, the doctor, the tools and/or workflow templates that are to be used or other things. In this way, when a user is using the integrated MRCS, the appropriate images are associated with the patient, body part etc, without the user having to weed through multiple studies/series manually. Further detailed information concerning workflow templates can be found in co-pending U.S. patent application Ser. No. 12/196,099, entitled "Workflow Template Management for Medical Image Data Processing," filed Aug. 21, 2008, which is incorporated by reference herein in its entirety.

The tag can be from a pre-defined list (predetermined preference tags). Alternatively, if the user does not find a reasonable tag in the list, the user may define a new tag (custom tags), as well as associations appropriate to that tag (tools to be opened etc.). Any user created tag can also be used for other images/studies/series.

Tags can also be extracted from the image data themselves. For example, the scans contain information on the body part (a skull can be seen, or the heart, etc.), contrast (based on brightness, contrast, etc.), the procedure, the weight of the patient, the sex of the patient, the ailment, whether there is a table or info on the table on which the patient is lying, the number of images in a study, etc. Depending on the sophistication of the algorithm, significant amounts of information can be gleaned from the images themselves. From this information, tags can be created which allow the MRCS to open the correct images and tools in the correct context.

Associating tags with an image/series/study could be done manually or automatically. The association can be done as soon as an image(s) is uploaded to the medical imaging processing server, or can be done on request. The advantage of doing it automatically when the image(s) is uploaded is that the tags can be developed in the background, or at night or during other low usage times so that the integration with the MRCS can be much quicker. The advantage of doing the association on request is that fewer resources are used and a user can influence the tag creation, possibly making it more accurate. In addition, adding tags manually allows the algorithm to be dynamic vs. static. In other words, the algorithm can "learn" which tags are more likely to be associated with which image types.

Manually associating tags with an image series/study may require particular security levels. For example, some users may be able to create a new custom tag, while some users may only be able to assign a tag. Some users may not be able to do either. A tag may be private, associated with a group, public etc.

In one embodiment, the tags discussed above, which are associated with the image data, are then used by the MRCS to open up the correct image(s) and tools. For example, if a tag is "body part=heart" and a tag is "ailment=stenosis" and a tag is "patient ID=12345", this image data will be available when a doctor opens MRCS (such as EMR or clinical trial software) and he/she is looking at patient 12345. If the doctor drills down to a particular date, or body part, or ailment etc. which corresponds to the heart, this image data will be visible to him/her. If the doctor drills down to sunburn, this image would likely be configured to not be visible, since it is not associated with the sunburn ailment.

This same type of contextual integration could be done with any of the tags associated with the image data. The same could be done with the tools, so only certain tools are visible or are configured in a certain way based on the image tags. In the example above, the tools associated with cardiovascular disease would likely be the ones to be available when the heart image was being viewed.

Figure 7:
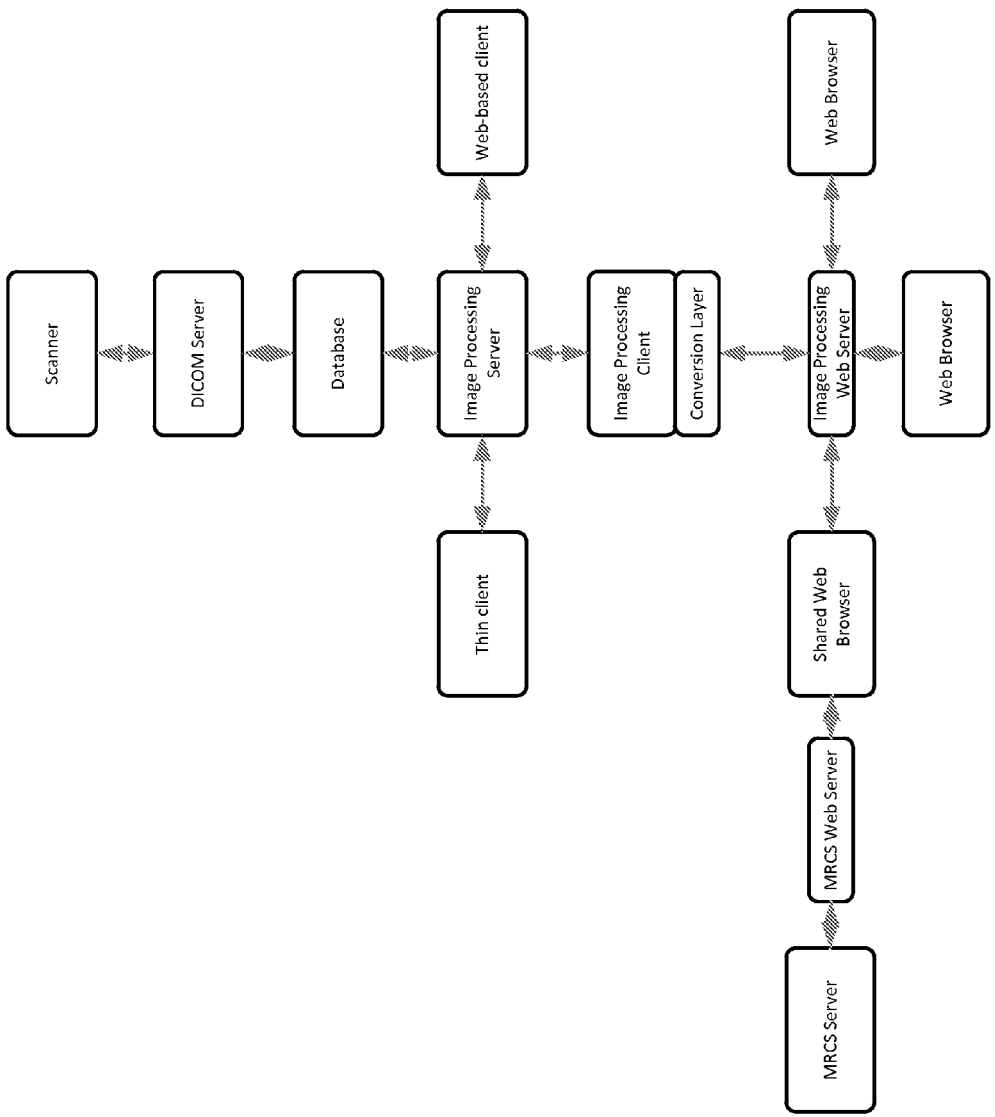
FIG. 7 illustrates a web-based architecture of image processing software according to another embodiment of the invention.

FIG. 7 illustrates an image processing system according to another embodiment of the invention. The MRCS server may reside physically in a different location from the image processing server, although they may be in the same location, for example, in a hospital or medical center. The box labeled "shared web browser" represents the GUI of the integrated medical software, examples of which have been shown in FIGS. 4A-4G and 5A-5D. The shared web browser is installed on a computer, mobile device or other hardware. The shared web browser in FIG. 7 can incorporate two or more different software packages, including EMR software, clinical trials software, dictation software, research software, radiology information system (RIS) software, picture archiving and communication system (PACS) software or other types of software.

Figure 8:
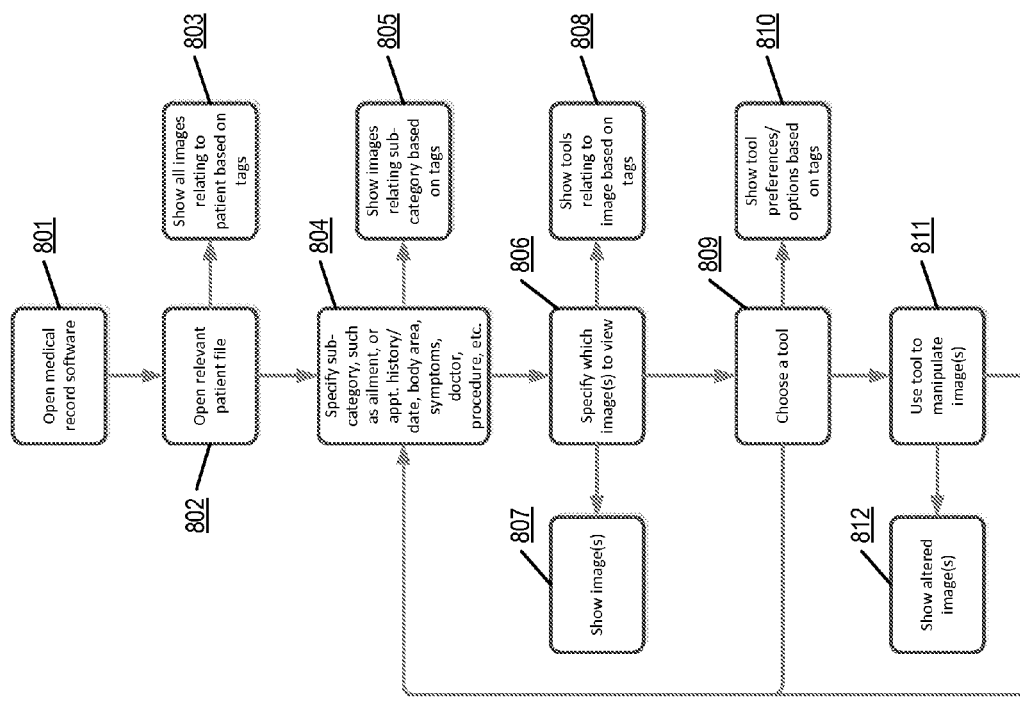
FIG. 8 illustrates a flow diagram illustrating a process performed by integrated medical record software according to one embodiment.

FIG. 8 is a flow diagram illustrating a method performed by integrated medical record software (MRS) according to one embodiment. Method 800 may be performed by MRS 107 of FIG. 1. Referring to FIG. 8, MRS is generally patient-centric so the user is entering or viewing information for a particular patient. After opening the MRS software itself (block 801), the user finds the patient she is looking for and opens the patient's file (block 802). This may be done by clicking on a link indicating the patient's name, ID or other means. The patient file, or screen, may automatically show images relating to the patient (block 803). These images are linked to the patient's record or file based on tags. In this case, the tag may be the patient ID.

The patient screen may also show several subcategories (block 804), such as ailments, appointment history/dates, body areas, symptoms, treating doctor, procedures etc. These may be shown as links, buttons, tabs or by other appropriate means. Once a subcategory is selected, images relating only to that subcategory may be shown (block 805). For example, if the user selects a particular appointment date, the user may only see images collected on that date. As another example, if the user selects the body part, head, only images relating to the patient's head may be shown. The subset of images which are visible is again determined by the image tags. More than one image or image series may be visible within any given subcategory. If the user then chooses an image/series/study to view 806, only that image/series/study is now visible 807.

In addition, only tools which are relevant to that image/study/series may be available/visible (block 808). Tools may also be visible based on user preferences). If a particular tool is chosen (809), it is possible that the preferences associated with this tool may be limited by user preferences and/or image tags (810). For example, if a user chooses the "zoom" tool, the image may automatically zoom to a specific zoom level, based on either user preferences (one user might like 50%) or image tags. For example, images of the colon may be shown at a particular suitable magnification to start with, while images of the brain may be shown at another magnification. The tool/tools may be used to manipulate the image(s) (block 811). The altered image view can be viewed and/or saved (block 812). For example, a user may want to highlight certain areas of the vasculature of the heart where there are potential stenoses.

Figure 9:
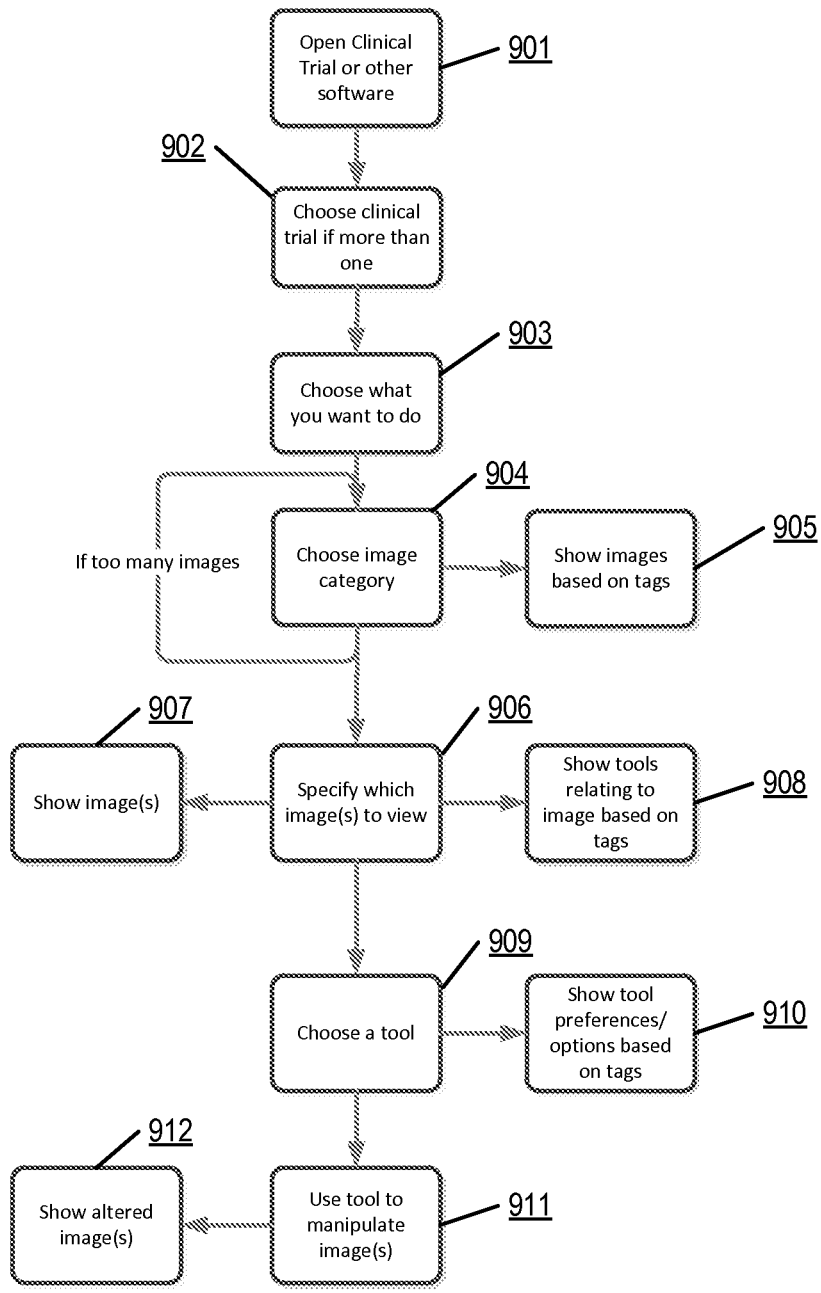
FIG. 9 illustrates a flow diagram illustrating a process performed by integrated clinical trial software according to one embodiment.

FIG. 9 is a flow diagram illustrating a method performed by integrated clinical trial software according to one embodiment. Method 900 may be performed by CTS 107 of FIG. 1. Referring to FIG. 9, CTS is clinical trial-centric so the user is generally viewing, or possibly entering, data relating to a clinical trial as a whole. However, sometimes the user may want to drill down to the individual patient level. For example, if the data includes images, measurements or other data may need to be derived from the image data. Also, it may be necessary to view the individual data points relating to the image data.

After opening the software itself (block 901), if the user is involved in more than one clinical trial, she will choose the appropriate clinical trial (block 902). The user will then be presented with a screen relating to the clinical trial as a whole (block 902). This may appear as a dashboard or other format. If the user wants to drill down, she will likely be presented with various next step choices depending on the study design (block 903). For example, image viewing/processing may be used for quality control, to make sure the image data was received OK, Or image viewing/processing could be used by a participating physician to interpret the images according to the clinical trial protocol, Or image viewing/processing could be used for auditing to check the work done, Or image viewing/processing could be used to compare two or more interpretations in the case of a double-blind study, Or image viewing/processing could be used for presentations and follow-up work to manage the imaging data in the trial database and to capture relevant images for reports etc, In order to drill down to the individual images that the user wants to view, she may need to choose an image category, such as patient ID, doctor, study center/site, date, etc.

Once an image category is chosen (block 904), images relating to that category may be shown based on image tags (block 905). Images may not be shown at this level if there are too many to show reasonably.

If the user wants to drill down further, she can drill down further within the various image categories. Once the user gets down to a category which is narrow enough, images relating to that category (by image tag) will be shown. More than one image or image series may be visible within any given category. If the user then chooses an image/series/study to view (block 906), only that image/series/study is now visible (block 907). In addition, only tools which are relevant to that image/study/series may be available or visible (block 908). Tools may also be visible based on user preferences. More than one image/series/study can be chosen in block 906.

If a particular tool is chosen (block 909), it is possible that the preferences associated with this tool may be limited by user preferences and/or image tags (block 910). For example, if a user chooses a "zoom" tool, the image may automatically zoom to a specific zoom level, based on either user preferences (one user might like 50%) or image tags. For example, images of the colon may be shown at a particular suitable magnification to start with, while images of the brain may be shown at another magnification. The tool/tools may be used to manipulate the image(s) (block 911). The altered image view can be viewed and/or saved (block 912). For example, a user may want to highlight certain areas of the vasculature of the heart where there are potential stenoses.

Note that most of the image rendering operations are performed by the image processing server over a network (e.g., Internet). When a user interacts with the integrated MRCS at a client device, commands and responses are exchanged between the client system and the server. For example, when a user select a subcategory, category identifying information (e.g., tags) of the subcategory is transmitted to the image processing server. Based on the category identifying information, the image processing server identifies one or more images that are associated with the requested sub-category and transmits those images to the client device to be displayed by the integrated MRCS.

Similarly, when the user zooms in a first image currently displayed (e.g., via a zoom-in tool icon), a zoom in command may be transmitted to the server. Based on the command, the server renders the image and generates a zoomed in version of the image. The new image is then transmitted to the integrated MRCS for display.

According to some embodiments, a variety of image processing tools can be provided at the integrated MRCS. The following are examples of medical image processing tools that may be included as part of the image processing described above. These examples are provided for illustrative purposes and not intended to be a limitation of the present invention.

Vessel Analysis tools may include a comprehensive vascular analysis package for CT and MR angiography capable of a broad range of vascular analysis tasks, from coronary arteries to aortic endograft planning and more general vascular review, including carotid and renal arteries. Auto-centerline extraction, straightened view, diameter and length measurements, CPR and axial renderings, and Vessel Track mode for automated thin-slab MIP may be included.

Calcium scoring tools may include Semi-automated identification of coronary calcium with Agatston, volume and mineral mass algorithms. An integrated reporting package with customization options may be included.

Time-dependent analysis tools may include time-resolved planar or volumetric 4D brain perfusion examinations acquired with CT or MR. The TDA tools may support color or mapping of various parameters such as mean enhancement time and enhancement integral, with semi-automated selection of input function and baseline, to speed analysis. TDA tools may support rapid automated processing of dynamic 4D area-detector CT examinations to ensure interpretation within minutes of acquisition.

CT/CTA (Computed tomography angiography) subtraction tools are used in the removal of non-enhancing structures (e.g. bone) from CT angiography examinations, the CT/CTA option includes automatic registration of pre- and post-contrast images, followed by a dense-voxel masking algorithm which removes high-intensity structures (like bone and surgical clips) from the CTA scan without increasing noise, aiding with the isolation of contrast-enhanced vascular structures.

Lobular decomposition tools identify tree-like structures within a volume of interest, e.g. a scan region containing a vascular bed, or an organ such as the liver. The LD tool can then identifies sub-volumes of interest based on proximity to a given branch of the tree or one of its sub-branches. Research applications include the analysis of the lobular structure of organs.

General Enhancement & Noise Treatment with Low Exposure tools may include an advanced volumetric filter architecture applying noise management techniques to improve the effectiveness of 3D, centerline, contouring and segmentation algorithms even when source image quality is not optimum.

The Spherefinder tools perform automated analysis of volumetric examinations to identify the location of structures with a high sphericity index (characteristics exhibited by many nodules and polyps). Spherefinder is often used with Lung or Colon CT scans to identify potential areas of interest.

Segmentation, analysis & tracking tools support analysis and characterization of masses and structures, such as solitary pulmonary nodules or other potential lesions. Tools may identify and segment regions of interest, and then apply measurement criteria, such as RECIST and WHO, leading to tabulated reporting of findings and follow-up comparison. Display and management of candidate markers from optional detection engines may be supported, including Spherefinder.

Time volume analysis tools may provide automated calculation of ejection fraction from a chamber in rhythmic motion, such as a cardiac ventricle. A fast and efficient workflow may be included to enable the user to identify the wall boundaries of interest (e.g. epicardium and endocardium) and, based on these user-confirmed regions of interest, to report ejection fraction, wall volume (mass) and wall thickening from multi-phasic CT data. Tabulated reporting output is included.

Maxillo-facial tools support the analysis and visualization of CT examinations of the Maxillo-facial region, these tools apply the CPR tool to generate "panoramic" projections in various planes and of various thicknesses, and cross-sectional MPR views at set increments along the defined curve plane.

Applicable to endoluminal CT or MR investigations such as colon, lungs, or blood vessels, the Flythrough tools supports side-by-side review, painting of previously-viewed areas, percent coverage tracking, and multiple screen layouts including forward, reverse, fisheye and flat volume rendered views. Tools for contrast subtraction, "Cube View", and integrated contextual reporting may be supported. Display and management of candidate markers from optional detection engines may be supported, including iNtuition's Spherefinder.

The Volumetric Histogram tools allow a volume of interest to be segmented and analyzed for composition. Research applications include the analysis of low-attenuation regions of the lungs, threshold-based division of tumors into voxel populations, investigation of thrombosed vessels or aneurysms, or other pathology.

Findings workflow tools provide a framework for tracking findings across serial examinations. A database holds measurements and key images, and provides support for structured comparisons and tabulated reporting of findings over time, such as the RECIST 1.1 approach for presenting serial comparisons. The Annotation and Image Markup (AIM) XML schema may be supported, for automated integration with voice-recognition systems or clinical databases, and Word-based reports may be derived from the database.

With these tools, any two CT, PET, MR or SPECT series, or any two-series combination thereof can be overlaid with one assigned a semi-transparent color coding and the other shown in grayscale and volume rendering for anatomical reference. Automatic registration is provided and subtraction to a temporary series or to a saved, third series is possible. Support for PET/MR visualization is included.

Certain MR examinations (for example, Breast MR) involve a series of image acquisitions taken over a period of time, where certain structures become enhanced over time relative to other structures. These tools feature the ability to subtract a pre-enhancement image from all post-enhancement images to emphasize visualization of enhancing structures (for example, vascular structures and other enhancing tissue). Time-dependent region-of-interest tools may be provided to plot time-intensity graphs of a given region.

Parametric mapping tools are an enhancement to the Multi-Phase MR tools, the parametric mapping option pre-calculates overlay maps where each pixel in an image is color-coded depending on the time-dependent behavior of the pixel intensity. As an example, this tool can be used in Breast MR to speed identification and investigation of enhancing regions.

The MultiKv tools provide support for Dual Energy and Spectral Imaging acquisitions from multiple vendors, providing standard image processing algorithms such as segmentation or contrast suppression, as well as generic toolkits for precise analysis and development of new techniques.

Figure 10:
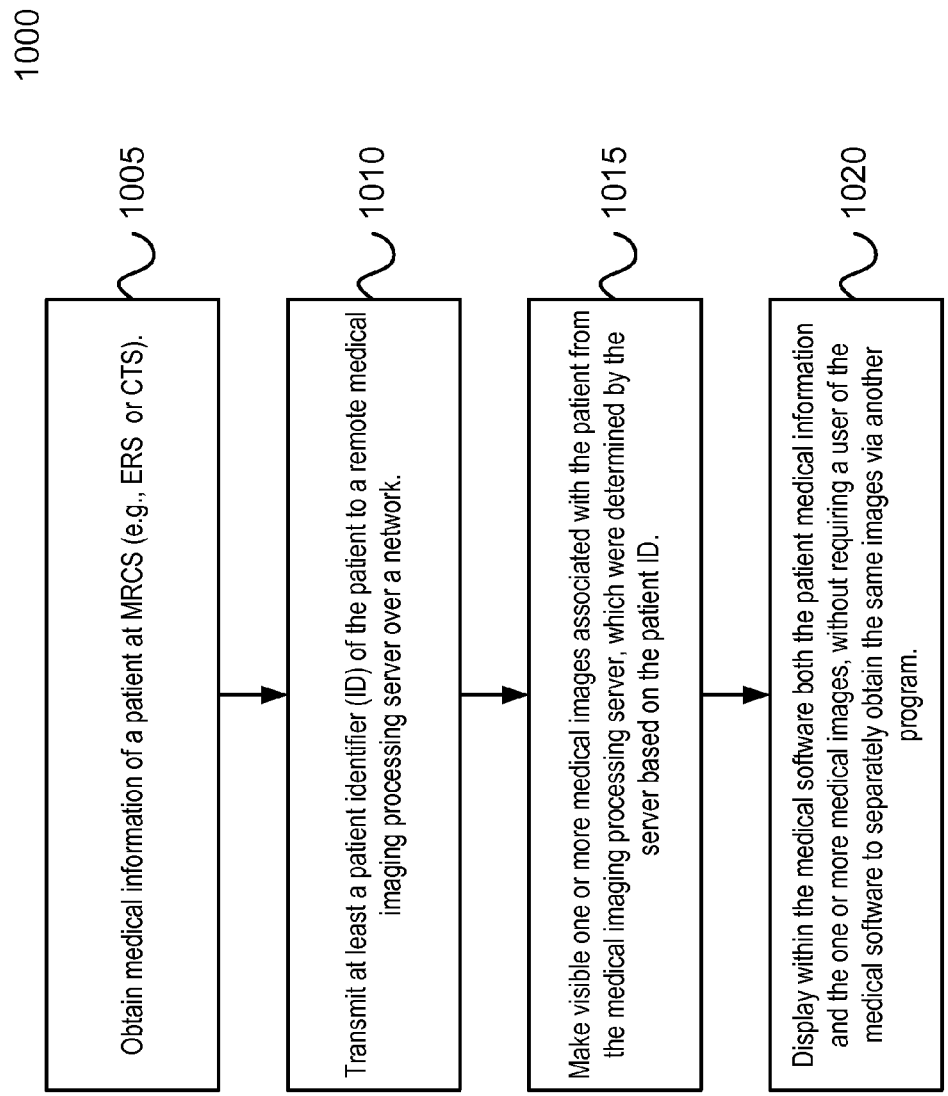
FIG. 10 is a flow chart that illustrates an exemplary method displaying within the MRCS, both the patient information and associated image(s) without requiring the opening of another software program.

FIG. 10 is a flow diagram that illustrates a method of displaying within the MRCS, both the patient information and associated image(s) according to one embodiment. Method 1000 may be performed by MRCS 107 of FIG. 1. Referring to FIG. 10, at block 1005, the medical information of a patient is obtained at integrated MRCS. In one embodiment, the medical information is obtained from a remote server similar to the medical data server 115 of FIG. 3. In such an embodiment, the user of the integrated MRCS may be required to log onto the remote medical data server, such as MRCS server 115, with proper security credentials, e.g., a valid user ID and password to be authenticated by access control system 116.

At block 1010, the integrated medical software transmits a portion of the obtained medical information to a remote medical imaging processing server over a network. In one embodiment, the transmitted medical information includes at least a patient ID of the patient. At block 1015, one or more medical images associated with the patient ID is made visible within the integrated MRCS. In one embodiment, the medical images that are associated with the patient ID are identified by the remote medical imaging processing server.

At block 1020, the integrated medical software displays within its GUI both the patient medical information and the one or more medical images, without requiring a user of the medical software to separately obtain the same images via another program (e.g., separate manual login or login via another program). In one embodiment, the GUI is the same window as the integrated medical software window. In an alternate embodiment, the GUI is a separate window from the integrated medical software window.

Figure 11:
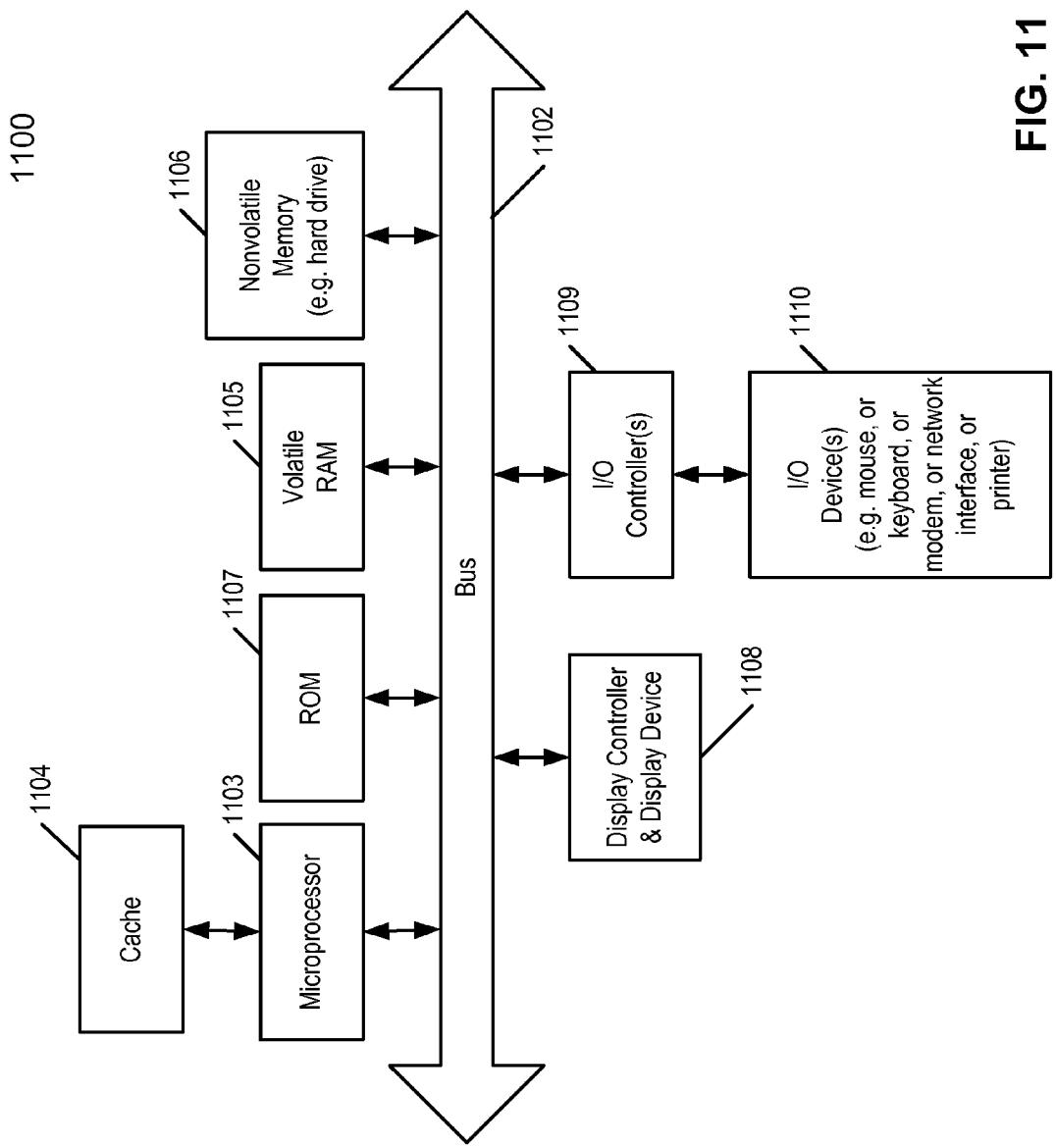
FIG. 11 is a block diagram illustrating a data processing system.

FIG. 11 is a block diagram of a data processing system, which may be used with one embodiment of the invention. For example, the system 1100 may be used as part of a server or a client as shown in FIG. 1. Note that while FIG. 11 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used with the present invention.

As shown in FIG. 11, the computer system 1100, which is a form of a data processing system, includes a bus or interconnect 1102 which is coupled to one or more microprocessors 1103 and a ROM 1107, a volatile RAM 1105, and a non-volatile memory 1106. The microprocessor 1103 is coupled to cache memory 1104. The bus 1102 interconnects these various components together and also interconnects these components 1103, 1107, 1105, and 1106 to a display controller and display device 1108, as well as to input/output (I/O) devices 1110, which may be mice, keyboards, modems, network interfaces, printers, and other devices which are well-known in the art.

Typically, the input/output devices 1110 are coupled to the system through input/output controllers 1109. The volatile RAM 1105 is typically implemented as dynamic RAM (DRAM) which requires power continuously in order to refresh or maintain the data in the memory. The non-volatile memory 1106 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 11 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 1102 may include one or more buses connected to each other through various bridges, controllers, and/or adapters, as is well-known in the art. In one embodiment, the I/O controller 1109 includes a USB (Universal Serial Bus) adapter for controlling USB peripherals. Alternatively, I/O controller 1109 may include an IEEE-1394 adapter, also known as FireWire adapter, for controlling FireWire devices.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding figures may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

In the foregoing specification, embodiments of the invention have been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A computer-implemented method performed by a medical record and/or clinical trial software (MRCS) client, the method comprising:
receiving, by the MRCS client executed by a processor within a data processing system, medical information of a patient from a medical data server over a network;
displaying at least a portion of medical information of the patient within the MRCS client, wherein the displayed medical information includes a first portion describing a first medical procedure associated with a first body part of the patient;
in response to a first user input selecting the first portion of the displayed medical information from a user operating the MRCS client, automatically extracting a first procedure identifier (ID) identifying the first medical procedure associated with the first body part of the patient;
transmitting a first request to a medical imaging processing server over the network, wherein the first request includes a patient ID of the patient and the first procedure ID identifying the first medical procedure associated with the first body part;
receiving a first set of one or more medical images from the medical imaging processing server over the network, wherein the one or more medical images of the first set are associated with the first medical procedure of the patient based on the patient ID and the first procedure ID;
displaying, within a single instance of the MRCS client, both the first portion of patient medical information and the first set of one or more medical images rendered by a medical image processing server;
displaying, within the single instance of the MRCS client, a first set of icons representing a first set of image processing tools, which when activated by a user, allow an image to be manipulated by the imaging processing server, wherein the first set of image processing tools is a subset of a plurality of image processing tools selected by the image processing server based on the first procedure ID;
in response to a second user input selecting a first image of the first set and a first image processing tool from the first set of icons, transmitting a second request to the image processing server to perform a measurement on the first image using the first image processing tool, wherein the second request includes a first image ID identifying the selected first image and a first tool ID identifying the first image processing tool;
in response to a measurement result of the first image from the image processing server, displaying the measurement result within the MRCS client while the first image is concurrently displayed; and
transmitting the measurement result to the medical data server to be stored in a persistent storage device of the medical data server, wherein the measurement result is associated with the first medical procedure of a medical data entry corresponding to the patient, such that the measurement result is retrieved subsequently from the medical data server as part of the first portion of the medical information of the patient.

2. The method of claim 1, further comprising:
in response to the first user input selecting the first portion of the displayed medical information, extracting one or more keywords from the first portion of the medical information; and
transmitting the one or more keywords as part of the first request to the image processing server, wherein at least one of the image processing tools is determined by the image processing server based on the one or more keywords.

3. The method of claim 1, further comprising:
determining a user preference of the user utilizing the MRCS client with respect to the first portion of the medical information of the patient; and
displaying the set of icons in a manner within the MRCS client based on the user preference of the user.

4. The method of claim 3, wherein the user preference is determined based on previous user interactions with the first portion of the medical information from the user.

5. The method of claim 1, wherein the second request is to request the image processing server to measure a size of a tumor of the first image, and wherein the measurement result is transmitted to the medical data server as medical image metadata to be associated with the first portion of the medical information stored therein.

6. The method of claim 5, further comprising:
receiving a body mass index (BMI) of the patient from the medical data server as a part of medical information of the patient; and
transmitting the BMI of the patient to the image processing server to be stored therein and associated with the patient, wherein the measurement of the tumor is performed further based on the BMI of the patient.

7. The method of claim 6, further comprising:
retrieving from the medical data server a list of measurements of the tumor of the first body part that were performed by the image processing server over a predetermined period of time; and
displaying the list of measurements of the tumor of the first body part as a part of the first portion of medical information.

8. The method of claim 1, wherein the first set of image processing tools comprises a computed tomography angiography (CTA) subtraction tool to remove a high density structure from an image.

9. The method of claim 8, wherein the first set of image processing tools further comprises a vessel analysis tool to perform an auto-centerline extraction, a straighten view, a diameter and length measurement on a blood vessel.

10. The method of claim 9, wherein the first set of image processing tools further comprises a flythrough tool to provide a side-by-side review, painting of a previously-viewed area, percentage coverage tracking, and multiple screen layouts.

11. A non-transitory machine-readable medium storing instructions that, when executed, cause a processing device to perform operations of a medical record and/or clinical trial software (MRCS) client, the operations comprising:
receiving, by the MRCS client executed by a processor within a data processing system, medical information of a patient from a medical data server over a network;
displaying at least a portion of medical information of the patient within the MRCS client, wherein the displayed medical information includes a first portion describing a first medical procedure associated with a first body part of the patient;
in response to a first user input selecting the first portion of the displayed medical information from a user operating the MRCS client, automatically extracting a first procedure identifier (ID) identifying the first medical procedure associated with the first body part of the patient;
transmitting a first request to a medical imaging processing server over the network, wherein the first request includes a patient ID of the patient and the first procedure ID identifying the first medical procedure associated with the first body part;
receiving a first set of one or more medical images from the medical imaging processing server over the network, wherein the one or more medical images of the first set are associated with the first medical procedure of the patient based on the patient ID and the first procedure ID;
displaying, within a single instance of the MRCS client, both the first portion of patient medical information and the first set of one or more medical images rendered by a medical image processing server;
displaying, within the single instance of the MRCS client, a first set of icons representing a first set of image processing tools, which when activated by a user, allow an image to be manipulated by the imaging processing server, wherein the first set of image processing tools is a subset of a plurality of image processing tools selected by the image processing server based on the first procedure ID;
in response to a second user input selecting a first image of the first set and a first image processing tool from the first set of icons, transmitting a second request to the image processing server to perform a measurement on the first image using the first image processing tool, wherein the second request includes a first image ID identifying the selected first image and a first tool ID identifying the first image processing tool;
in response to a measurement result of the first image from the image processing server, displaying the measurement result within the MRCS client while the first image is concurrently displayed; and
transmitting the measurement result to the medical data server to be stored in a persistent storage device of the medical data server, wherein the measurement result is associated with the first medical procedure of a medical data entry corresponding to the patient, such that the measurement result is retrieved subsequently from the medical data server as part of the first portion of the medical information of the patient.

12. The non-transitory machine-readable medium of claim 11, wherein the operations further comprise:
in response to the first user input selecting the first portion of the displayed medical information, extracting one or more keywords from the first portion of the medical information; and
transmitting the one or more keywords as part of the first request to the image processing server, wherein at least one of the image processing tools is determined by the image processing server based on the one or more keywords.

13. The non-transitory machine-readable medium of claim 11, wherein the operations further comprise:
determining a user preference of the user utilizing the MRCS client with respect to the first portion of the medical information of the patient; and
displaying the set of icons in a manner within the MRCS client based on the user preference of the user.

14. The non-transitory machine-readable medium of claim 13, wherein the user preference is determined based on previous user interactions with the first portion of the medical information from the user.

15. The non-transitory machine-readable medium of claim 11, wherein the second request is to request the image processing server to measure a size of a tumor of the first image, and wherein the measurement result is transmitted to the medical data server as medical image metadata to be associated with the first portion of the medical information stored therein.

16. The non-transitory machine-readable medium of claim 15, wherein the operations further comprise:
receiving a body mass index (BMI) of the patient from the medical data server as a part of medical information of the patient; and
transmitting the BMI of the patient to the image processing server to be stored therein and associated with the patient, wherein the measurement of the tumor is performed further based on the BMI of the patient.

17. The non-transitory machine-readable medium of claim 16, wherein the operations further comprise:
retrieving from the medical data server a list of measurements of the tumor of the first body part that were performed by the image processing server over a predetermined period of time; and
displaying the list of measurements of the tumor of the first body part as a part of the first portion of medical information.

18. The non-transitory machine-readable medium of claim 11, wherein the first set of image processing tools comprises a computed tomography angiography (CTA) subtraction tool to remove a high density structure from an image.

19. The non-transitory machine-readable medium of claim 18, wherein the first set of image processing tools further comprises a vessel analysis tool to perform an auto-centerline extraction, a straighten view, a diameter and length measurement on a blood vessel.

20. The non-transitory machine-readable medium of claim 19, wherein the first set of image processing tools further comprises a flythrough tool to provide a side-by-side review, painting of a previously-viewed area, percentage coverage tracking, and multiple screen layouts.

21. A data processing system comprising:
a processor; and
a memory storing instructions representing a medical record and/or clinical trial software (MRCS) client, which when executed from the memory, cause the processor to perform operations, the operations including
receiving, by the MRCS client executed by a processor within a data processing system, medical information of a patient from a medical data server over a network,
displaying at least a portion of medical information of the patient within the MRCS client, wherein the displayed medical information includes a first portion describing a first medical procedure associated with a first body part of the patient,
in response to a first user input selecting the first portion of the displayed medical information from a user operating the MRCS client, automatically extracting a first procedure identifier (ID) identifying the first medical procedure associated with the first body part of the patient,
transmitting a first request to a medical imaging processing server over the network, wherein the first request includes a patient ID of the patient and the first procedure ID identifying the first medical procedure associated with the first body part,
receiving a first set of one or more medical images from the medical imaging processing server over the network, wherein the one or more medical images of the first set are associated with the first medical procedure of the patient based on the patient ID and the first procedure ID,
displaying, within a single instance of the MRCS client, both the first portion of patient medical information and the first set of one or more medical images rendered by a medical image processing server,
displaying, within the single instance of the MRCS client, a first set of icons representing a first set of image processing tools, which when activated by a user, allow an image to be manipulated by the imaging processing server, wherein the first set of image processing tools is a subset of a plurality of image processing tools selected by the image processing server based on the first procedure ID,
in response to a second user input selecting a first image of the first set and a first image processing tool from the first set of icons, transmitting a second request to the image processing server to perform a measurement on the first image using the first image processing tool, wherein the second request includes a first image ID identifying the selected first image and a first tool ID identifying the first image processing tool,
in response to a measurement result of the first image from the image processing server, displaying the measurement result within the MRCS client while the first image is concurrently displayed, and
transmitting the measurement result to the medical data server to be stored in a persistent storage device of the medical data server, wherein the measurement result is associated with the first medical procedure of a medical data entry corresponding to the patient, such that the measurement result is retrieved subsequently from the medical data server as part of the first portion of the medical information of the patient.

22. The system of claim 21, wherein the operations further comprise:
in response to the first user input selecting the first portion of the displayed medical information, extracting one or more keywords from the first portion of the medical information; and
transmitting the one or more keywords as part of the first request to the image processing server, wherein at least one of the image processing tools is determined by the image processing server based on the one or more keywords.

23. A computer-implemented method performed by a medical record and/or clinical trial software (MRCS) client, the method comprising:
receiving, by the MRCS client executed by a processor within a data processing system, medical information of a patient from a medical data server over a network;
displaying at least a portion of medical information of the patient within the MRCS client, wherein the displayed medical information includes a first portion describing a first medical procedure associated with a first body part of the patient;

in response to a first user input selecting the first portion of the displayed medical information from a user operating the MRCS client, automatically identifying and extracting one or more keywords from the first portion of the medical information;

transmitting a first request to a medical imaging processing server over the network, wherein the first request includes a patient ID of the patient and the one or more keywords associated with the first portion of the medical information;

receiving a first set of one or more medical images from the medical imaging processing server over the network, wherein the one or more medical images of the first set are associated with the first medical procedure of the patient based on the patient ID and the first procedure ID;

displaying, within a single instance of the MRCS client, both the first portion of patient medical information and the first set of one or more medical images rendered by a medical image processing server;

displaying, within the single instance of the MRCS client, a first set of icons representing a first set of image processing tools, which when activated by a user, allow an image to be manipulated by the imaging processing server, wherein the first set of image processing tools is a subset of a plurality of image processing tools selected by the image processing server based on the one or more keywords;

in response to a second user input selecting a first image of the first set and a first image processing tool from the first set of icons, transmitting a second request to the image processing server to perform a measurement on the first image using the first image processing tool, wherein the second request includes a first image ID identifying the selected first image and a first tool ID identifying the first image processing tool;

in response to a measurement result of the first image from the image processing server, displaying the measurement result within the MRCS client while the first image is concurrently displayed; and transmitting the measurement result to the medical data server to be stored in a persistent storage device of the medical data server, wherein the measurement result is associated with the first medical procedure of a medical data entry corresponding to the patient, such that the measurement result is retrieved subsequently from the medical data server as part of the first portion of the medical information of the patient.

24. The method of claim 23, further comprising:

determining a user preference of the user utilizing the MRCS client with respect to the first portion of the medical information of the patient; and displaying the set of icons in a manner within the MRCS client based on the user preference of the user.

* * * * *